United States Patent
Farris et al.

(10) Patent No.: US 11,141,342 B2
(45) Date of Patent: Oct. 12, 2021

(54) WEARABLE ROBOTIC DEVICE

(71) Applicant: Parker-Hannifin Corporation, Cleveland, OH (US)

(72) Inventors: Ryan Farris, Solon, OH (US); Mike Clausen, Turlock, CA (US); Edgar Wilson, Toledo, OH (US)

(73) Assignee: Parker-Hannifin Corporation, Cleveland, OH (US)

( * ) Notice: Subject to any disclaimer, the term of this patent is extended or adjusted under 35 U.S.C. 154(b) by 94 days.

(21) Appl. No.: 16/360,790

(22) Filed: Mar. 21, 2019

(65) Prior Publication Data

US 2019/0216673 A1 Jul. 18, 2019

Related U.S. Application Data

(62) Division of application No. 15/119,403, filed as application No. PCT/US2015/023624 on Mar. 31, 2015, now Pat. No. 10,537,488.

(Continued)

(51) Int. Cl.
*A61H 3/00* (2006.01)
*A61H 1/02* (2006.01)
(Continued)

(52) U.S. Cl.
CPC .............. *A61H 3/00* (2013.01); *A61F 5/0102* (2013.01); *A61F 5/0111* (2013.01); *A61H 1/024* (2013.01);
(Continued)

(58) Field of Classification Search
CPC ...................................................... A61H 3/00
See application file for complete search history.

(56) References Cited

U.S. PATENT DOCUMENTS 4,564,365 A 1/1986 Winer et al.
4,640,301 A * 2/1987 Battiston, Sr. ........... A61H 3/00
135/67

(Continued)

FOREIGN PATENT DOCUMENTS

EP 1637116 3/2006
JP 2010/0000204 A 1/2010
(Continued)

OTHER PUBLICATIONS

International Search Report and Written Opinion for International Application No. PCT/US2015/023624, dated Oct. 5, 2015.

(Continued)

*Primary Examiner* — Jacqueline Woznicki
(74) *Attorney, Agent, or Firm* — Renner, Otto, Boisselle & Sklar, LLP

(57) ABSTRACT

A self-aligning, self-drawing coupler for coupling body assemblies together improves usability of a wearable robotic device. A self-contained removable actuator cassette improves the ease of manufacture and of replacing parts in the field. A tensioning retention system designed for one handed operation makes donning and doffing a wearable robotic device easier. A two-stage attachment system increases the range of sizes a wearable robotic device will fit. A removable, integrated ankle-foot orthotic system makes donning and doffing a wearable robotic device easier. An infinitely adjustable, integrated ankle-foot orthotic system increases the range of sizes a wearable robotic device will fit. A manually-removable hip-wing attachment system makes field changes easier, and protecting such a system from inadvertent disengagement during operation increases safety.

5 Claims, 35 Drawing Sheets

Related U.S. Application Data

(60) Provisional application No. 61/973,129, filed on Mar. 31, 2014.

(51) Int. Cl.
  *B25J 9/00* (2006.01)
  *A61F 5/01* (2006.01)
  *B25J 9/10* (2006.01)

(52) U.S. Cl.
  CPC .......... *A61H 1/0244* (2013.01); *B25J 9/0006* (2013.01); *B25J 9/104* (2013.01); *B25J 9/1045* (2013.01); *A61F 5/0123* (2013.01); *A61F 5/0127* (2013.01); *A61F 2005/0155* (2013.01); *A61H 2003/007* (2013.01); *A61H 2201/0107* (2013.01); *A61H 2201/0176* (2013.01); *A61H 2201/0192* (2013.01); *A61H 2201/1215* (2013.01); *A61H 2201/164* (2013.01); *A61H 2201/165* (2013.01); *A61H 2201/1628* (2013.01); *A61H 2201/5058* (2013.01)

(56) References Cited

U.S. PATENT DOCUMENTS

| | | | |
|---|---|---|---|
| 5,271,649 A | 12/1993 | Gromotka | |
| 6,666,796 B1* | 12/2003 | MacCready, Jr. | A61F 5/0102 135/65 |
| 7,628,766 B1 | 12/2009 | Kazerooni et al. | |
| 2006/0052731 A1* | 3/2006 | Shimada | A61H 3/00 602/5 |
| 2006/0064047 A1* | 3/2006 | Shimada | A61H 1/0255 602/23 |
| 2006/0079964 A1 | 4/2006 | Perkins et al. | |
| 2006/0276728 A1* | 12/2006 | Ashihara | A61H 1/0262 601/5 |
| 2008/0154165 A1* | 6/2008 | Ashihara | A61H 1/0255 602/23 |
| 2008/0156363 A1* | 7/2008 | Ikeuchi | B25J 9/0006 135/65 |
| 2009/0036815 A1* | 2/2009 | Ido | A61H 3/008 602/23 |
| 2009/0048686 A1* | 2/2009 | Ikeuchi | B25J 9/0006 623/27 |
| 2009/0199883 A1* | 8/2009 | Hiki | A61H 3/008 135/65 |
| 2010/0010639 A1* | 1/2010 | Ikeuchi | B25J 9/0006 623/24 |
| 2010/0036302 A1* | 2/2010 | Shimada | A61F 5/0102 602/16 |
| 2010/0076360 A1* | 3/2010 | Shimada | A61F 5/0102 602/23 |
| 2010/0125229 A1* | 5/2010 | Rudolph | A61B 5/1121 602/16 |
| 2010/0271051 A1* | 10/2010 | Sankai | A61H 1/0262 324/679 |
| 2010/0298746 A1 | 11/2010 | Shimizu et al. | |
| 2011/0112447 A1* | 5/2011 | Hsiao-Wecksler | A61H 3/008 601/33 |
| 2011/0168485 A1 | 7/2011 | Takashi et al. | |
| 2012/0172770 A1* | 7/2012 | Almesfer | A61H 1/0255 601/35 |
| 2012/0316476 A1 | 12/2012 | Hideo et al. | |
| 2012/0316477 A1 | 12/2012 | Hamaya et al. | |
| 2013/0046218 A1* | 2/2013 | Wiggin | A61F 5/0102 602/16 |
| 2013/0197408 A1* | 8/2013 | Goldfarb | A61H 3/00 601/35 |
| 2013/0331744 A1* | 12/2013 | Kamon | A61H 3/00 601/35 |
| 2014/0005798 A1 | 1/2014 | Bache et al. | |
| 2015/0045703 A1* | 2/2015 | Strausser | A61H 1/0255 601/35 |
| 2015/0272810 A1* | 10/2015 | Teng | A61H 1/0244 601/34 |
| 2016/0184166 A1* | 6/2016 | Takenaka | A61F 2/60 623/27 |
| 2016/0270997 A1* | 9/2016 | Little | A61H 1/0266 |
| 2016/0278961 A1* | 9/2016 | Sutti | A61F 5/0127 |
| 2017/0014297 A1* | 1/2017 | Grygorowicz | B25J 9/0006 |
| 2017/0143573 A1* | 5/2017 | Boulanger | A61H 1/0244 |
| 2017/0165087 A1* | 6/2017 | Kim | A61F 2/6607 |
| 2017/0231853 A1* | 8/2017 | Auger | A61F 5/0195 623/40 |
| 2018/0055712 A1* | 3/2018 | Gayral | A61H 1/0266 |
| 2018/0092797 A1* | 4/2018 | Uzzo | A61H 9/0078 |
| 2018/0104075 A1* | 4/2018 | Mooney | A61H 1/0262 |
| 2018/0161188 A1* | 6/2018 | Zistatsis | A61H 1/0244 |
| 2018/0200134 A1* | 7/2018 | Tsai | A61H 1/0262 |
| 2018/0280180 A1* | 10/2018 | Amari | A61H 1/0237 |
| 2018/0289578 A1* | 10/2018 | Suzuki | A61F 5/0195 |
| 2019/0015286 A1* | 1/2019 | Glaister | A61H 1/0237 |
| 2019/0192373 A1* | 6/2019 | Vouga | A61H 1/0262 |
| 2019/0254908 A1* | 8/2019 | Ortlieb | A61H 1/0244 |
| 2019/0282424 A1* | 9/2019 | Lerner | A61H 3/00 |
| 2019/0282428 A1* | 9/2019 | Belinkov | A61H 3/00 |
| 2019/0282430 A1* | 9/2019 | Zhang | A61H 1/00 |
| 2019/0328605 A1* | 10/2019 | van den Bogert | A61H 3/00 |
| 2020/0016020 A1* | 1/2020 | Mooney | A61H 3/00 |
| 2020/0191208 A1* | 6/2020 | Kim | F16D 3/223 |

FOREIGN PATENT DOCUMENTS

| | | |
|---|---|---|
| JP | 2010/0000205 A | 1/2010 |
| JP | 2010-110365 A | 5/2010 |
| JP | 2011-156344 A | 8/2011 |
| JP | 2011156344 | 8/2011 |
| KR | 2013-0045874 A | 5/2013 |
| KR | 20130045874 | 5/2013 |
| KR | 101325066 | 11/2013 |
| WO | WO 95/01141 | 1/1995 |
| WO | WO 2005/046536 | 5/2005 |
| WO | 2006/078871 | 7/2006 |
| WO | 2009/082249 | 7/2009 |
| WO | WO 2010/079862 | 7/2010 |
| WO | WO 2012/044621 | 4/2012 |
| WO | 2014/138872 A1 | 9/2014 |

OTHER PUBLICATIONS

International Preliminary Report on Patentability for International Application No. PCT/US2015/023624, dated Jul. 4, 2016.
Search Report issued by EPO for corresponding European patent application No. 19204421.2 dated Jan. 2, 2020.

* cited by examiner

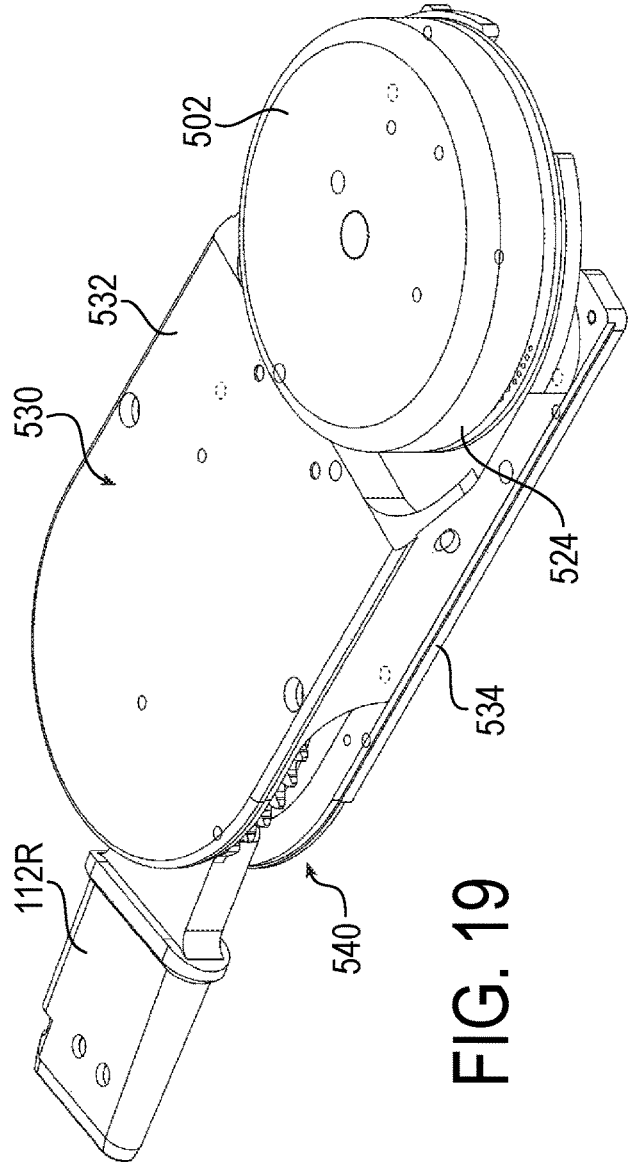
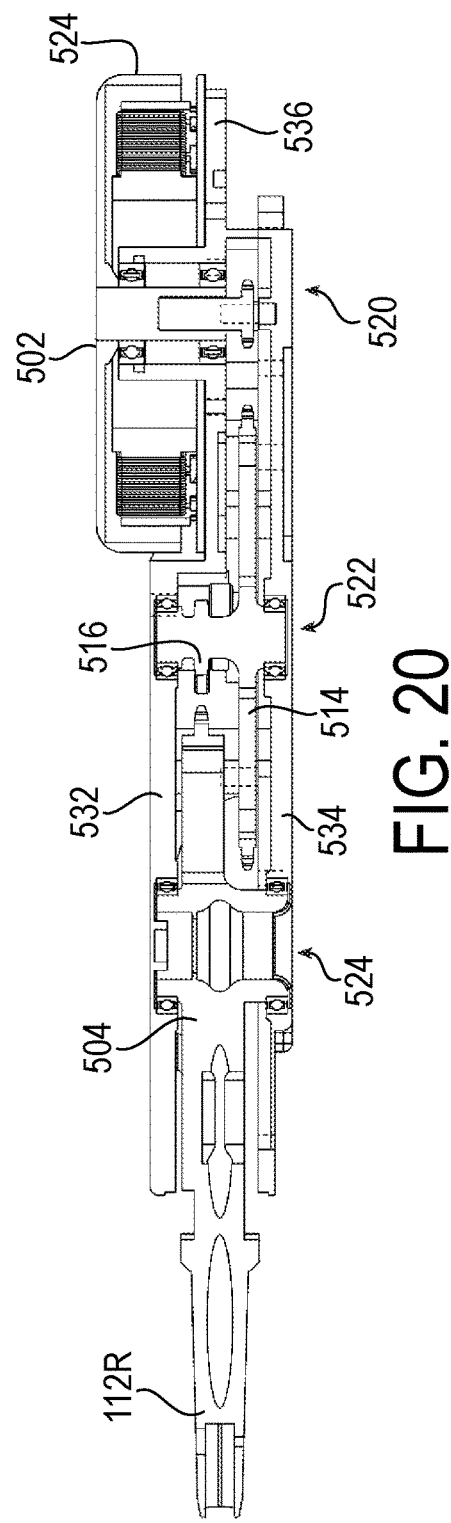

WEARABLE ROBOTIC DEVICE

RELATED APPLICATIONS

This application is a divisional of U.S. application Ser. No. 15/119,403 filed Aug. 17, 2016 which is a national phase of International Patent Application Serial No. PCT/US2015/023624 filed Mar. 31, 2015, which claims the benefit of U.S. Provisional Application No. 61/973,129 filed Mar. 31, 2014, which is hereby incorporated herein by reference.

FIELD OF INVENTION

The present invention relates generally to wearable robotic devices, and more particularly to improvements in operability to powered lower limb orthoses.

BACKGROUND

There are currently about 262,000 spinal cord injured (SCI) individuals in the United States, with roughly 12,000 new injuries sustained each year at an average age of injury of 40.2 years. Of these, approximately 44% (5300 cases per year) result in paraplegia. One of the most significant impairments resulting from paraplegia is the loss of mobility, particularly given the relatively young age at which such injuries occur. Surveys of users with paraplegia indicate that mobility concerns are among the most prevalent, and that chief among mobility desires is the ability to walk and stand. In addition to impaired mobility, the inability to stand and walk entails severe physiological effects, including muscular atrophy, loss of bone mineral content, frequent skin breakdown problems, increased incidence of urinary tract infection, muscle spasticity, impaired lymphatic and vascular circulation, impaired digestive operation, and reduced respiratory and cardiovascular capacities.

In an effort to restore some degree of legged mobility to individuals with paraplegia, several lower limb orthoses have been developed. The simplest form of passive orthotics are long-leg braces that incorporate a pair of ankle-foot orthoses (AFOs) to provide support at the ankles, which are coupled with leg braces that lock the knee joints in full extension. The hips are typically stabilized by the tension in the ligaments and musculature on the anterior aspect of the pelvis. Since almost all energy for movement is provided by the upper body, these (passive) orthoses require considerable upper body strength and a high level of physical exertion, and provide very slow walking speeds. The hip guidance orthosis (HGO), which is a variation on long-leg braces, incorporates hip joints that rigidly resist hip adduction and abduction, and rigid shoe plates that provide increased center of gravity elevation at toe-off, thus enabling a greater degree of forward progression per stride. Another variation on the long-leg orthosis, the reciprocating gait orthosis (RGO), incorporates a kinematic constraint that links hip flexion of one leg with hip extension of the other, typically by means of a push-pull cable assembly. As with other passive orthoses, the user leans forward against the stability aid while un weighting the swing leg and utilizing gravity to provide hip extension of the stance leg. Since motion of the hip joints is reciprocally coupled through the reciprocating mechanism, the gravity-induced hip extension also provides contralateral hip flexion (of the swing leg), such that the stride length of gait is increased. One variation on the RGO incorporates a hydraulic-circuit-based variable coupling between the left and right hip joints. Experiments with this variation indicate improved hip kinematics with the modulated hydraulic coupling.

In order to decrease the high level of exertion associated with passive orthoses, the use of powered orthoses has been previously investigated, which incorporate actuators and an associated power supply to assist with locomotion. These orthoses have been shown to increase gait speed and decrease compensatory motions, relative to walking without powered assistance, however, the development of these orthoses is still in its infancy

SUMMARY OF INVENTION

A self-aligning, self-drawing coupler for coupling body assemblies together improves usability of a wearable robotic device. A self-contained removable actuator cassette improves the ease of manufacture and of replacing parts in the field. A tensioning retention system designed for one handed operation makes donning and doffing a wearable robotic device easier. A two-stage attachment system increases the range of sizes a wearable robotic device will fit. A removable, integrated ankle-foot orthotic system makes donning and doffing a wearable robotic device easier. An infinitely adjustable, integrated ankle-foot orthotic system increases the range of sizes a wearable robotic device will fit. A manually-removable hip-wing attachment system makes field changes easier, and protecting such a system from inadvertent disengagement during operation increases safety.

According to one aspect of the invention, a wearable robotic device includes a thigh assembly for attachment to a thigh of a user having a first portion of a self-aligning, self-drawing coupler; a hip assembly for attachment to a hip region of the user having a second portion of the self-aligning, self-drawing coupler; and a latch configured to draw the first portion of the self-aligning, self-drawing coupler to a latched position relative to the second portion of the self-aligning, self-drawing coupler.

Optionally, the first portion of the self-aligning, self-drawing coupler includes a tapered male portion receivable in a complimentary tapered female portion of the second portion of the self-aligning, self drawing coupler.

Optionally, a length of the tapered male portion is longer than a widest width portion.

Optionally, the tapered male portion includes a taper angle of between 1 and 10 degrees.

Optionally, latch includes a manually operable lever.

Optionally, the first portion of the self-aligning, self-drawing coupler includes a male portion receivable in a complimentary female portion of the second portion of the self-aligning, self-drawing coupler, one of the male or female portions including a friction-reducing surface.

Optionally, the friction-reducing surface is a Teflon coating.

Optionally, the thigh assembly extends downward along a longitudinal thigh axis from the first portion of the self-aligning, self-drawing coupler.

Optionally, the thigh assembly includes a motive device.

Optionally, the hip assembly extends upward and laterally away from the second portion of the self-aligning, self-drawing coupler, and partially circumscribes a vertical body axis.

Optionally, the hip assembly extends laterally away from the second portion of the self-aligning, self-drawing coupler, and includes a second portion of a second self-aligning, self-drawing coupler.

Optionally, the wearable robotic device includes a second thigh assembly for attachment of a second thigh of the user and including a first portion of a second self-aligning, self-drawing coupler.

Optionally, the thigh assembly is rotatable with respect to the hip assembly when the thigh assembly is coupled to the hip assembly by the self-aligning, self-drawing coupler.

Optionally, the wearable robotic device includes a power source and a motive device powered by the power source and configured to rotate at least a portion of the thigh assembly relative to at least a portion of the hip assembly.

Optionally, the thigh assembly includes the motive device.

Optionally, the second portion of the self-aligning, self-drawing coupler includes a linkage device configured to transmit motion from an input lever to a latch element.

Optionally, the linkage device includes an input link, a floating link, an output link, and a ground link.

Optionally, the linkage device includes a lever as the input link.

Optionally, the linkage device includes a resilient latch element coupled at a first end to the output link.

Optionally, the resilient latch element has a second end slidably captured in a guideway for controlling motion of the latch element during operation.

Optionally, the guideway includes a generally straight draw portion aligned with the female portion of the coupler, and an engagement portion extending laterally away from the draw portion for guiding the latch element into and out of engagement with a corresponding latch element of the second portion of the coupler.

Optionally, the resilient latch element provides a biasing force in the linkage mechanism for locking the linkage mechanism in an over-center configuration.

Optionally, the over-center position is a locked open position.

Optionally, the over-center position is a locked closed position.

According to another aspect, a wearable robotic device includes a first body assembly having a first portion of a self-aligning, self-drawing coupler; a second body assembly having a second portion of the self-aligning, self-drawing coupler; a power source; a motive device powered by the power source and configured to move at least a portion of the first or second body assembly relative to the other of the first or second body assembly; and a latch configured to draw the first portion of the self-aligning, self-drawing coupler to a latched position relative to the second portion of the self-aligning, self-drawing coupler.

Optionally, one of the first or second body assembly includes the motive device.

Optionally, the first body assembly is a thigh assembly configured to be worn by a user and extends downward along a longitudinal thigh axis from the first portion of the self-aligning, self-drawing coupler.

Optionally, the thigh assembly includes the motive device.

Optionally, the second body assembly is a hip assembly configured to be worn by a user and extends upward and laterally away from the second portion of the self-aligning, self-drawing coupler, and partially circumscribes a vertical body axis.

Optionally, the first portion of the self-aligning, self-drawing coupler includes a tapered male portion receivable in a complimentary tapered female portion of the second portion of the self-aligning, self drawing coupler.

Optionally, a length of the tapered male portion is longer than a widest width portion.

Optionally, the tapered male portion includes a taper angle of between 1 and 10 degrees.

Optionally, the latch includes a manually operable lever.

Optionally, the first portion of the self-aligning, self-drawing coupler includes a male portion receivable in a complimentary female portion of the second portion of the self-aligning, self drawing coupler, one of the male or female portions including a friction-reducing surface.

Optionally, the friction-reducing surface is a Teflon coating.

Optionally, the hip assembly extends laterally away from the second portion of the self-aligning, self-drawing coupler, and includes a second portion of a second self-aligning, self-drawing coupler.

Optionally, the wearable robotic device includes a second thigh assembly for attachment of a second thigh of the user and including a first portion of a second self-aligning, self-drawing coupler.

Optionally, the thigh assembly is rotatable with respect to the hip assembly when the thigh assembly is coupled to the hip assembly by the self-aligning, self-drawing coupler.

Optionally, the second portion of the self-aligning, self-drawing coupler includes a linkage device configured to transmit motion from an input lever to a latch element.

Optionally, the linkage device includes an input link, a floating link, an output link, and a ground link.

Optionally, the linkage device includes a lever as the input link.

Optionally, the linkage device includes a resilient latch element coupled at a first end to the output link.

Optionally, the resilient latch element has a second end slidably captured in a guideway for controlling motion of the latch element during operation.

Optionally, the guideway includes a generally straight draw portion aligned with the female portion of the coupler, and an engagement portion extending laterally away from the draw portion for guiding the latch element into and out of engagement with a corresponding latch element of the second portion of the coupler.

Optionally, the resilient latch element provides a biasing force in the linkage mechanism for locking the linkage mechanism in an over-center configuration.

Optionally, the over-center position is a locked open position.

Optionally, the over-center position is a locked closed position.

According to another aspect, a removable, self-contained, ovular actuator cassette receivable in a receptacle of a wearable robotic device includes: a first circular portion housing a motive device; a second circular portion longitudinally offset and longitudinally overlapping the first circular portion and housing a first portion of a drivetrain operatively coupled to and driven by the motive device; a third circular portion longitudinally offset from the first and second circular portions and longitudinally overlapping the second circular portion and housing a second portion of the drivetrain; an ovular housing supporting the motive device and drivetrain; and an output protruding from and rotatable with respect to the housing and driven by the drivetrain.

Optionally, the housing includes a top plate on which the motive device is mounted, the drive shaft of the motive device protruding through the top plate.

Optionally, the housing includes a bottom plate.

Optionally, the drive train is sandwiched between the top plate and the bottom plate.

Optionally, the motive device is mounted outside the top and bottom plates.

Optionally, a maximum depth of the cassette measured along a rotational axis of the motive device is less than a maximum width and a maximum length, the maximum width and maximum length being measured orthogonal to the depth and to each other.

Optionally, all rotational axes of the drivetrain are parallel to the rotational axis of the motive device.

Optionally, long sides of the ovular housing are straight and parallel with each other and tangentially terminate at curved end surfaces of the ovular housing.

Optionally, the cassette includes an output opening in the housing through which the output protrudes and slide covers disposed in the output opening and movable with the output to cover portions of the output opening not occupied by the output.

Optionally, the output includes a first portion of a coupler connectable to a complimentary portion of the coupler.

According to another aspect, a wearable robotic device includes a removable, self-contained actuator cassette including a power connector and a driven output; and an exoskeletal assembly including a receptacle for receiving and retaining the removable, self-contained actuator cassette.

Optionally, the driven output includes a first portion of a coupler connectable to a complimentary portion of the coupler.

Optionally, the removable, self-contained actuator cassette includes: a first circular portion housing a motive device; a second circular portion longitudinally offset and longitudinally overlapping the first circular portion and housing a first portion of a drivetrain operatively coupled to and driven by the motive device; a third circular portion longitudinally offset from the first and second circular portions and longitudinally overlapping the second circular portion and housing a second portion of the drivetrain; an ovular housing supporting the motive device and drivetrain; and wherein the output protrudes from and is rotatable with respect to the housing and driven by the drivetrain.

Optionally, the housing includes a top plate on which the motive device is mounted, the drive shaft of the motive device protruding through the top plate.

Optionally, the housing includes a bottom plate.

Optionally, the drive train is sandwiched between the top plate and the bottom plate.

Optionally, the motive device is mounted outside the top and bottom plates.

Optionally, a maximum depth of the cassette measured along a rotational axis of the motive device is less than a maximum width and a maximum length, the maximum width and maximum length being measured orthogonal to the depth and to each other.

Optionally, all rotational axes of the drivetrain are parallel to the rotational axis of the motive device.

Optionally, long sides of the ovular housing are straight and parallel with each other and tangentially terminate at curved end surfaces of the ovular housing.

Optionally, an exemplary wearable robotic device includes an output opening in the housing through which the output protrudes and slide covers disposed in the output opening and movable with the output to cover portions of the output opening not occupied by the output.

Optionally, the output includes a first portion of a coupler connectable to a complimentary portion of the coupler.

According to another aspect, a wearable robotic device includes: a first body assembly for attachment to a first portion of a user's body; a second body assembly for attachment to a second portion of the user's body; an actuator having first and second actuator portions respectively connected to the first and second body assemblies and configured to move the first and second body assembly relative each other; wherein the first body assembly includes an attachment device for attaching to the first portion of the user's body, the attachment device including a tensioning system for retention of the first body assembly to the first portion of the user's body, the tensioning system including a tensionable member and a tensioning member.

Optionally, the tensioning member includes a ratchet.

Optionally, the tensioning member includes a cable reel and the tensionable member includes a cable acted upon by the cable reel to tension the cable.

Optionally, the attachment device includes a strap releasably coupled at a first end to a first strap anchor of the one body assembly.

Optionally, the strap is releasably coupled at a second end to a second strap anchor of the one body assembly.

Optionally, the attachment point of the strap to the strap anchor is adjustable.

Optionally, the strap is an adjustable length strap.

Optionally, the attachment device is removably coupled to the first body assembly at one end of the attachment device by a buckle.

Optionally, the buckle is rotatable with respect to the first body assembly in two orthogonal directions.

According to another aspect, a wearable robotic device includes a first body assembly for attachment to a first portion of a user's body; a second body assembly for attachment to a second portion of the user's body; an actuator having first and second actuator portions respectively connected to the first and second body assemblies and configured to move the first and second body assembly relative each other; an attachment device for attaching to the first portion of the user's body, the attachment device including a tensioning system for retention of the first body assembly to the first portion of the user's body, including a coarse adjuster and a separate fine adjuster.

Optionally, the fine adjuster includes a tensioning member and a tensionable member.

Optionally, the tensioning member includes a ratchet.

Optionally, the tensioning member includes a cable reel and the tensionable member includes a cable acted upon by the cable reel to tension the cable.

Optionally, the tensioning system includes a strap releasably coupled at a first end to a first strap anchor of the one body assembly.

Optionally, the strap is releasably coupled at a second end to a second strap anchor of the one body assembly.

Optionally, the attachment point of the strap to the strap anchor is adjustable.

Optionally, the strap is an adjustable length strap.

Optionally, the attachment device is removably coupled to the first body assembly at one end of the attachment device by a buckle.

Optionally, the buckle is rotatable with respect to the first body assembly in two orthogonal directions.

According to another aspect, an ankle-foot orthosis securable to a user's leg for controlling ankle movement includes a plantar element of rigid, thin-sheeted material; a leg element having a lower portion made of rigid thin-sheeted material rigidly connected to and extending upwardly from the plantar element and an upper portion having a retention system to secure said upper portion to a leg; a first portion of a coupler for coupling the ankle-foot orthosis to a wearable robotic device.

Optionally, the lower portion of the leg element and the plantar element are adjustably coupled to the upper portion and wherein a distance between the first portion of the coupler and the plantar element is adjustable.

Optionally, the distance between the first portion of the coupler and the plantar element is infinitely adjustable between minimum and maximum distances Optionally, the first portion of the coupler extends upward from the leg element.

Optionally, the lower portion of the leg element is lockable with respect to the upper portion of the leg element by means of a cam lock.

Optionally, the cam lock is manually operable.

According to another aspect, a wearable robotic device includes a thigh assembly having a thigh retention system to secure the thigh assembly to a user's thigh; a lower leg assembly rotatably coupled to the thigh assembly at a hinge including: a lower leg retention system to secure the thigh assembly to a user's lower leg, a lower leg housing, a plantar element of rigid material, and a leg element made of rigid material having a lower portion rigidly connected to and extending upwardly from the plantar element. The lower portion of the leg element and the plantar element are adjustably coupled to the lower leg housing and wherein a distance between the hinge and the plantar element is adjustable.

Optionally, the plantar element is made of a thin-sheeted material.

Optionally, the leg element is made of a thin-sheeted material.

Optionally, the thigh assembly and lower leg assembly are coupled by a quick-connect coupler.

Optionally, the quick connect coupler comprises the first and second portions of the self-aligning, self-drawing coupler of any preceding claim.

Optionally, the distance between the first portion of the coupler and the plantar element is infinitely adjustable between minimum and maximum distances.

Optionally, the first portion of the coupler extends upward from the leg element.

Optionally, the lower portion of the leg element is lockable with respect to the upper portion of the leg element by means of a cam lock.

Optionally, the cam lock is manually operable.

According to another aspect, a wearable robotic device includes: a first body assembly attachable to a portion of a user's body; and a hip assembly attachable to a hip region of a user's body and coupled to the first body assembly and rotatable with respect to the first body assembly via a motive device housed in at least one of the first body assembly or the hip assembly, the hip assembly partially circumscribes a vertical body axis and includes a rigid housing and a removable attachment device attachable to the hip region of a user's body and removable from the rigid housing by operation of a removal mechanism, the hip assembly further includes a battery receptacle for receiving a battery, the battery receptacle being associated with the removal mechanism and the removal mechanism being positioned such that access to the removal mechanism is precluded when the battery is installed in the battery receptacle.

Optionally, the battery receptacle further includes electrical contacts for mating with corresponding electrical contacts of the battery.

Optionally, the removal mechanism is manually operable.

Optionally, the removal mechanism includes a quick-release hinge pin.

Optionally, the removal mechanism includes a central guide cylinder housing a spring longitudinally outwardly biasing first and second finger-operated pins slidably disposed on opposite longitudinal sides of the guide cylinder.

According to another aspect, a wearable robotic device includes a first body assembly attachable to a portion of a user's body; and a hip assembly attachable to a hip region of a user's body and coupled to the first body assembly and rotatable with respect to the first body assembly via a motive device housed in at least one of the first body assembly or the hip assembly, the hip assembly partially circumscribes a vertical body axis and includes a rigid housing and a removable attachment device attachable to the hip region of a user's body and removable from the rigid housing by operation of a manually operable removal mechanism.

Optionally, the hip assembly further includes a battery receptacle for receiving a battery.

Optionally, the battery receptacle is associated with the removal mechanism, the removal mechanism being positioned such that access to the removal mechanism is precluded when the battery is installed in the battery receptacle.

Optionally, the battery receptacle further includes electrical contacts for mating with corresponding electrical contacts of the battery.

Optionally, the removal mechanism includes a quick-release hinge pin.

Optionally, the removal mechanism includes a central guide cylinder housing a spring longitudinally outwardly biasing first and second finger-operated pins slidably disposed on opposite longitudinal sides of the guide cylinder.

Optionally, the removable attachment device includes a hooked hinge portion with an inner hook surface and an outer hook surface partially circumscribing a rotational axis of the attachment device, wherein the rigid housing includes a hinge pin, and wherein the inner surface of the hooked hinge portion engages with the hinge pin and the removable attachment device rotates around the hinge pin when attached to the rigid housing.

Optionally, the rigid housing includes a radially inward facing hinge guide surface radially offset from and partially circumscribing the hinge pin, and the outer hook surface engages the hinge guide surface such that the hooked hinge portion is sandwiched between the hinge pin and the hinge guide surface when the removable attachment device is attached to the rigid housing.

Optionally, the rigid housing includes a detachment pocket into which the hooked hinge portion may be slid to disengage the hooked hinge portion from the hinge pin to detach the removable attachment device from the rigid housing.

The foregoing and other features of the invention are hereinafter described in greater detail with reference to the accompanying drawings.

BRIEF DESCRIPTION OF THE DRAWINGS

FIG. 19 shows a perspective view of an exemplary actuator cassette;

FIG. 20 shows a cross-sectional view of an exemplary actuator cassette taken along the longitudinal direction;

DETAILED DESCRIPTION

Although the various embodiments will be discussed at times with respect to orthoses for providing mobility assistance for users with paraplegia, the various embodiments are not limited in this regard. The various embodiments are equally application to other applications. For example, these can include mobility assistance for users with other conditions other than paraplegia, rehabilitation and mobility assistance for stroke-impaired users, and mobility assistance for users with neuromuscular disabilities that impair legged mobility, to name a few, including human and non-human users. Further, embodiments may be applied to other wearable robotic devices such as strength-enhancing exoskeletons for use in military, construction, or other applications. Thus, the various embodiments can be applied to any applications in which mobility assistance or enhancement is needed, either permanently or temporarily.

Further, although the various embodiments will be generally described with respect to the exemplary orthosis described below, the various embodiments are not limited to this particular configuration. The various embodiments can be embodied in or used with any type of exoskeleton system, such as the orthosis described below and further illustrated in design application Ser. No. 29/486,534, the entire disclosure of which is hereby incorporated herein by reference herein, or the orthosis described in International Publication Number WO 2012/044621, the entire disclosure of which is hereby incorporated by reference herein.

The terms "exoskeleton system," "exoskeleton," and "wearable robotic device," as used herein, refer to any type of device that can be worn or otherwise attached to a user, where the device is configured to provide energy for motion and or support of the one or more portions of the user.

Figure 1:
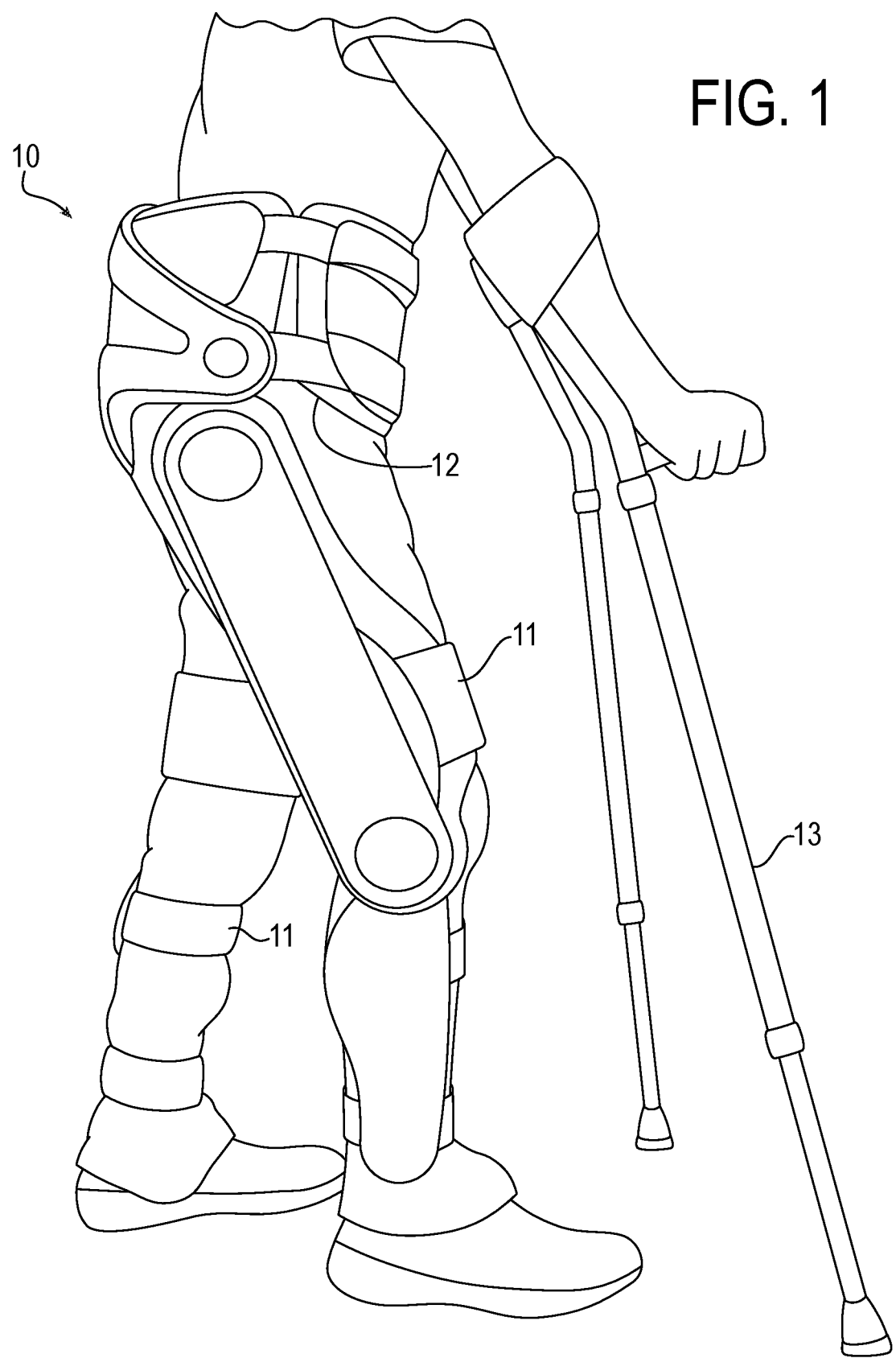
FIG. 1 shows a wearable robotic device being worn by a user.
Figure 2:
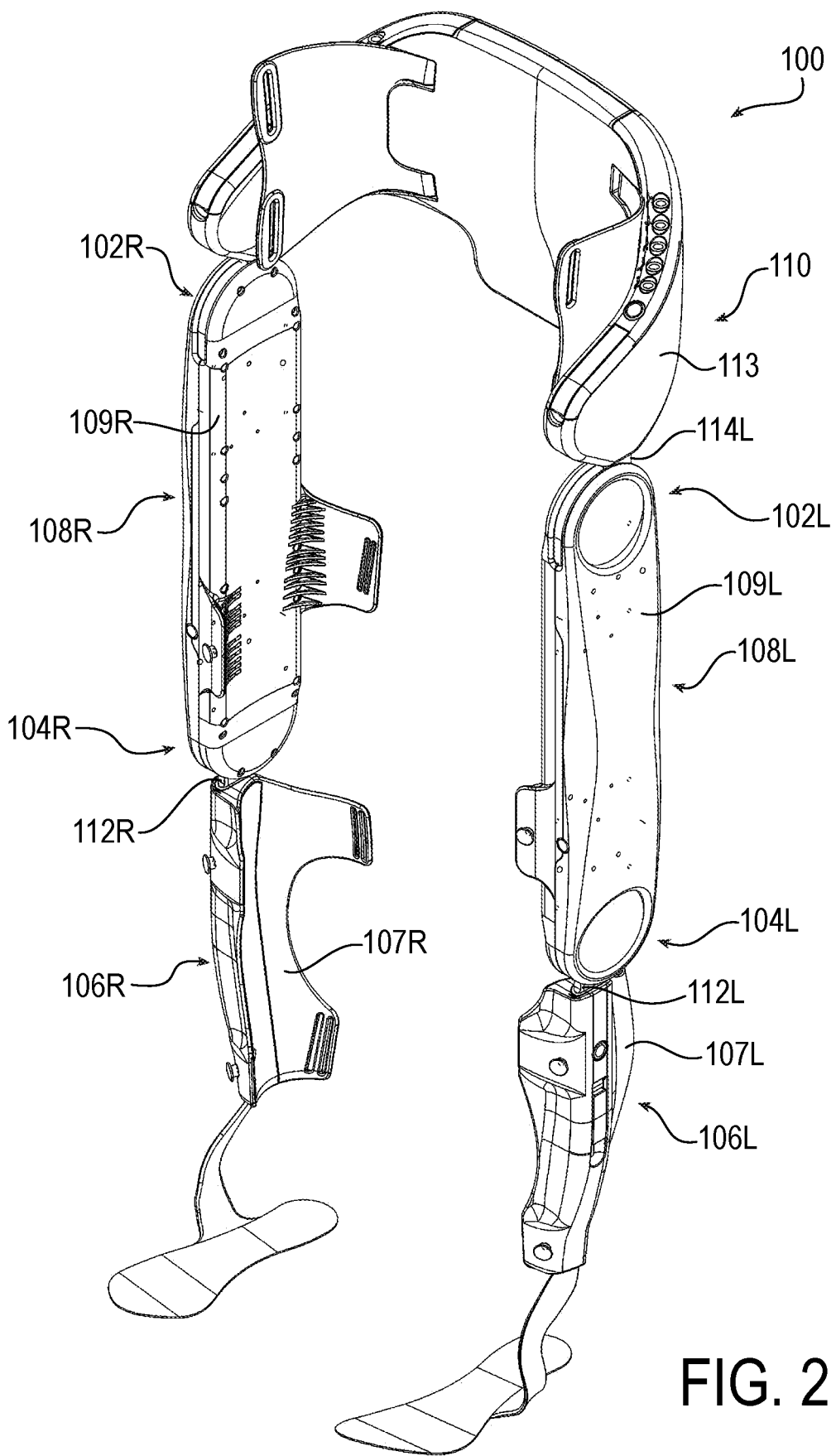
FIG. 2 shows a perspective view of an exemplary wearable robotic device in a standing position.

As show in FIG. 1, a wearable robotic device 10 can be worn by a user. To attach the device to the user, the device 10 can include attachment devices 11 for attachment of the device to the user via belts, loops, straps, or the like. Further, for comfort of the user, the device 10 can include padding 12 disposed along any surface likely to come into contact with the user. The device 10 can be used with a stability aid 13, such as crutches, a walker, or the like.

Figure 3:
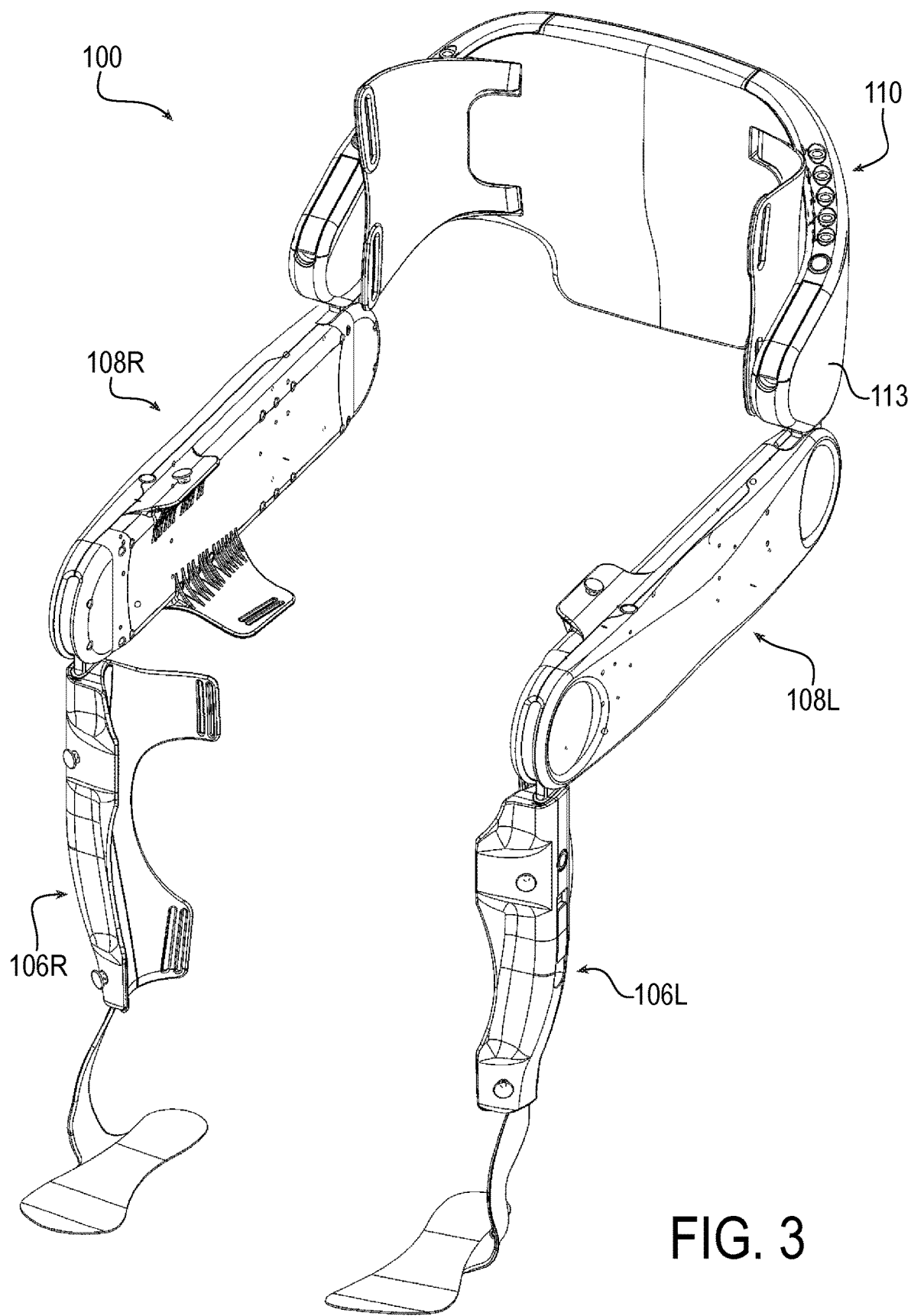
FIG. 3 shows a perspective view of the exemplary wearable robotic device in a seated position.
Figure 4:
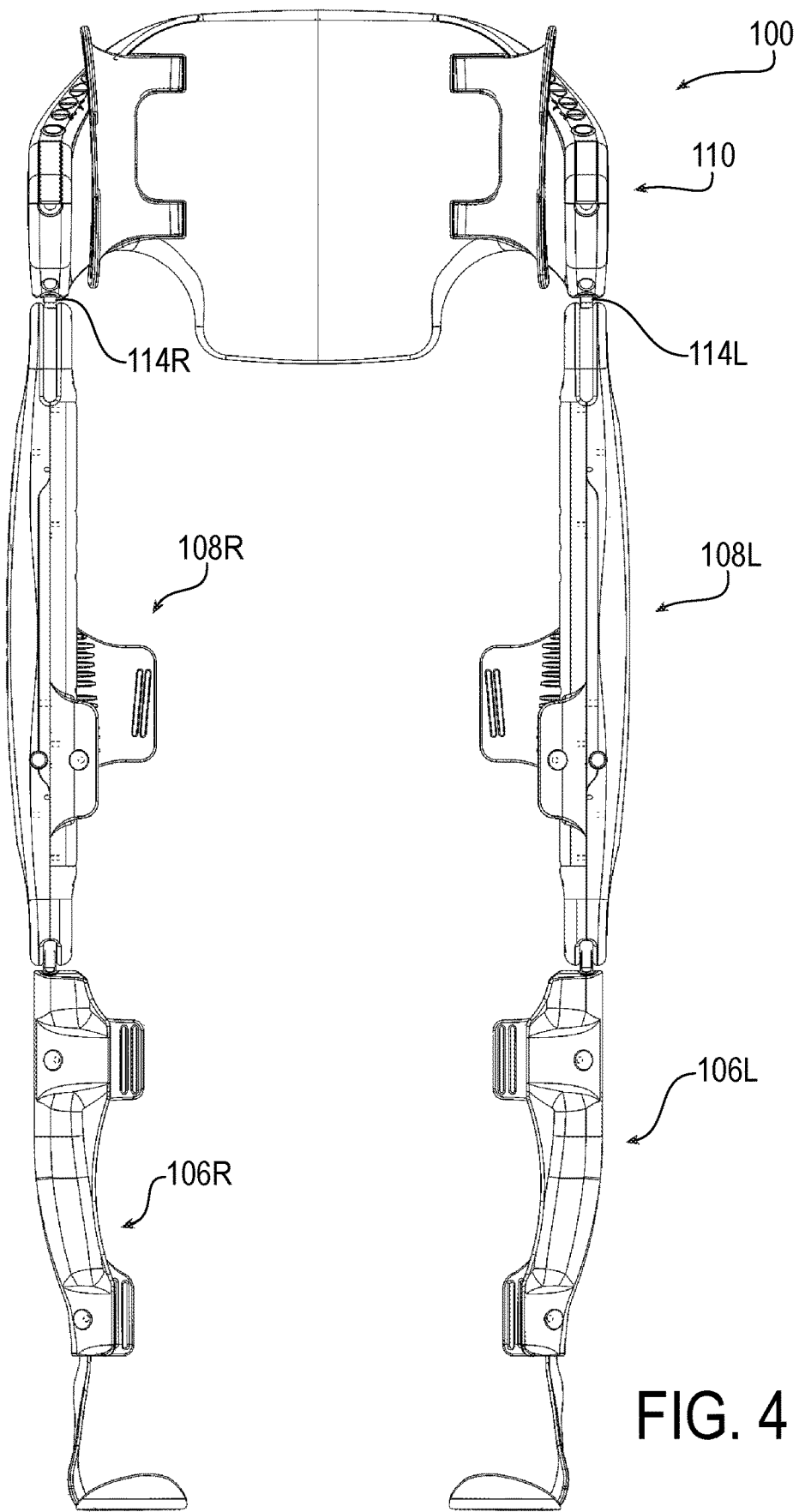
FIG. 4 shows a front view of the exemplary wearable robotic device in a standing position.
Figure 5:
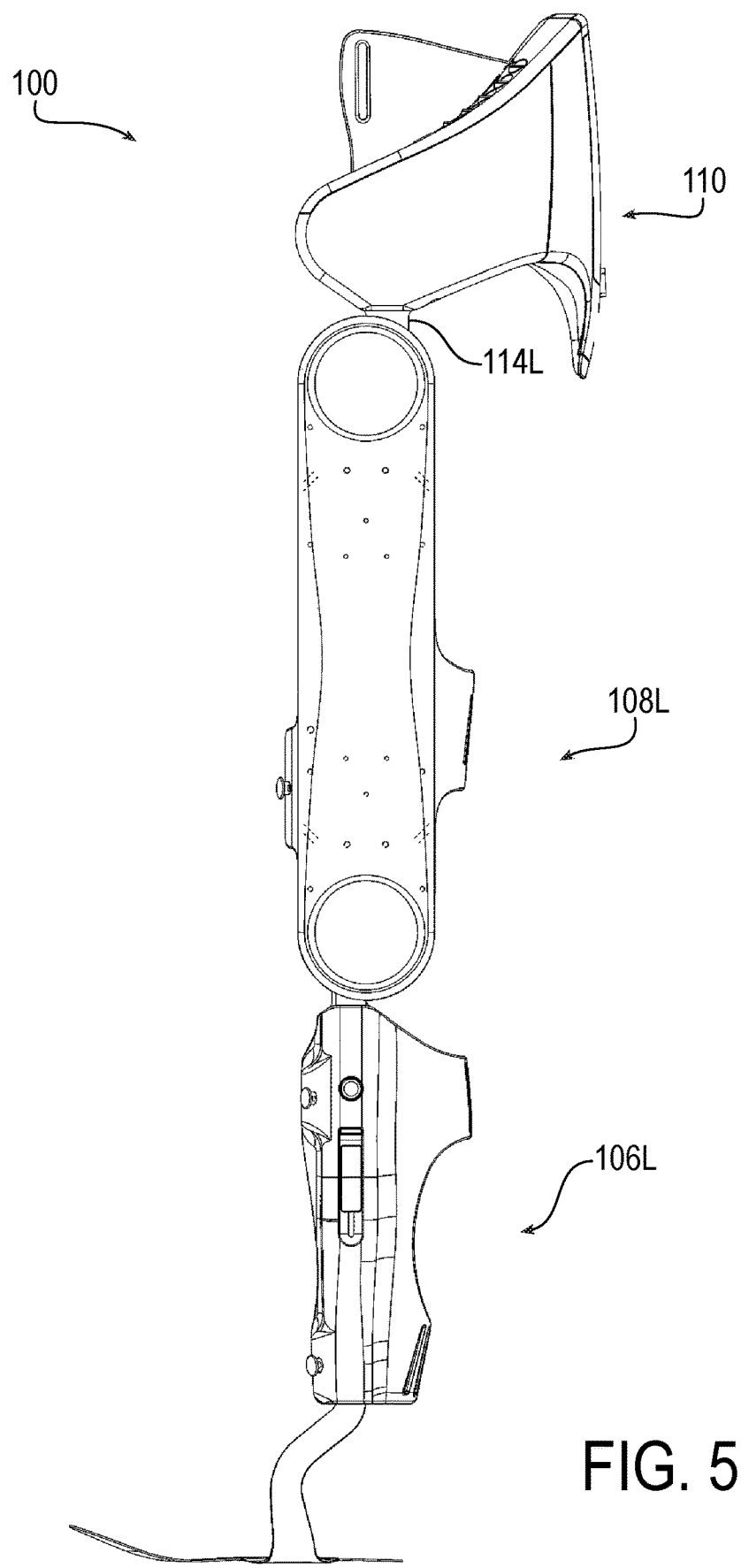
FIG. 5 shows a left view of the exemplary wearable robotic device in a standing position.
Figure 6:
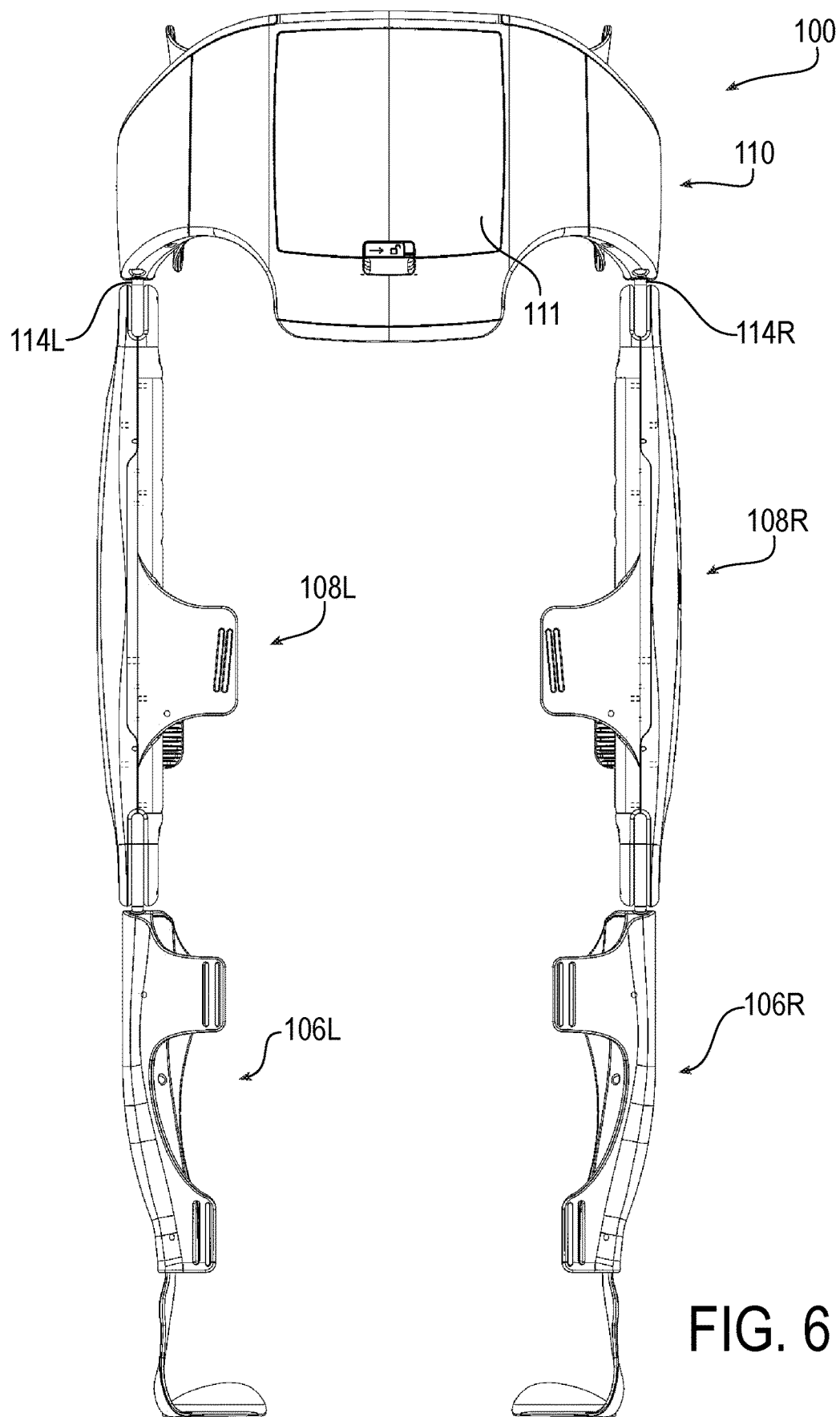
FIG. 6 shows a back view of the exemplary wearable robotic device in a standing position.

An exemplary wearable robotic device is illustrated as a powered lower limb orthosis 100 in FIGS. 2-6. Specifically, the orthosis 100 shown in FIGS. 2-6 incorporates four motive devices (for example, electric motors), which impose sagittal plane torques at each hip joint 102R, 102L and knee joint 104R, 104L. FIG. 1 shows the orthosis in a standing position while FIG. 3 shows the orthosis 100 in a seated position.

As seen in the figures, the orthosis contains five assemblies or modules, although one or more of these modules may be omitted and further modules may be added (for example, arm modules), which are: two lower leg assemblies (modules) 106R and 106L, two thigh assemblies 108R and 108L, and one hip assembly 110. Each thigh assembly 108R and 108L includes a thigh assembly housing 109R and 109L, respectively, and link, connector, or coupler 112R and 112L, respectively, extending from each of the knee joints 104R and 104L and configured for moving in accordance with the operation of the knee joints 104R and 104L to provide sagittal plane torque at the knee joints 104R and 104L.

The connectors 112R and 112L may be further configured for releasably mechanically coupling each of thigh assembly 108R and 108L to respective ones of the lower leg assemblies 106R and 106L. Further, each thigh assembly 108R and 108L also includes a link, connector, or coupler 114R and 114L, respectively, extending from each of the hip joints 102R and 102L and moving in accordance with the operation of the hip joints 102R and 102L to provide sagittal plane torque at the knee joints 104R and 104L. The connectors 114R and 114L may be further configured for releasably mechanically coupling each of thigh assemblies 108R and 108L to the hip assembly 110.

In some embodiments, the various components of device 100 can be dimensioned for the user. However, in other embodiments, the components can be configured to accommodate a variety of users. For example, in some embodiments, one or more extension elements can be disposed between the lower leg assemblies 106R and 106L and the thigh assemblies 108R and 108L to accommodate users with longer limbs. In other configurations, the lengths of the two lower leg assemblies 106R and 106L, two thigh assemblies 108R and 108L, and one hip assembly 110 can be adjustable. That is, thigh assembly housings 109R, 109L, the lower leg assembly housings 107R and 107L for the lower leg assemblies 106R, 106L, respectively, and the hip assembly housing 113 for the hip assembly 110 can be configured to allow the user or prosthestist to adjust the length of these components in the field. For example, these components can consist of slidable or movable sections that can be held in one or more positions using screws, clips, or any other types of fasteners. In view of the foregoing, the two lower leg assemblies 106R and 106L, two thigh assemblies 108R and 108L, and one hip assembly 110 can form a modular system allowing for one or more of the components of the orthosis 100 to be selectively replaced and for allowing an orthosis to be created for a user without requiring customized components. Such modularity can also greatly facilitate the procedure for donning and doffing the device.

In orthosis 100, each thigh assembly housing 109R, 109L may include substantially all the components for operating corresponding ones of the knee joints 104R, 104L and the hip joints 102R, 102L. In particular, each of thigh assembly housings 109R, 109L may include two motive devices (e.g., electric motors) which are used to drive the hip and knee articulations. However, the various embodiments are not limited in this regard and some components can be located in the hip assembly 110 and/or the lower leg assemblies 106R, 106L.

For example, a battery 111 for providing power to the orthosis can be located within hip assembly housing 113 and connectors 114R and 114L can also provide means for connecting the battery 111 to any components within either of thigh assemblies 108R and 108L. For example, the connectors 114R and 114L can include wires, contacts, or any other types of electrical elements for electrically connecting battery 111 to electrically powered components in thigh assemblies 108R and 108L. In the various embodiments, the placement of battery 111 is not limited to being within hip assembly housing 113. Rather, the battery can be one or more batteries located within any of the assemblies of orthosis 100.

Joint Coupler

Wearable robotic devices may be especially difficult to don and doff because of the weight of the device, and/or due to physical limitations of users due to some medical condition. In particular, it may be difficult to connect thigh assemblies to a hip assembly because one or more of these assemblies may be attached to the user's body already, and coupling may require both thigh assemblies to be coupled at the same time. Therefore, self-aligning and self-drawing couplers may ease donning and doffing of exemplary wearable robotic devices.

An exemplary coupler incorporates a tapered joint connection with a tapered top portion that interfaces with a mating tapered receptacle to tightly secure the portions in place. Embodiments of this mechanical connection could also include an electrical interconnect 195 for power and/or other communication; these may include redundant contacts.

Figure 7:
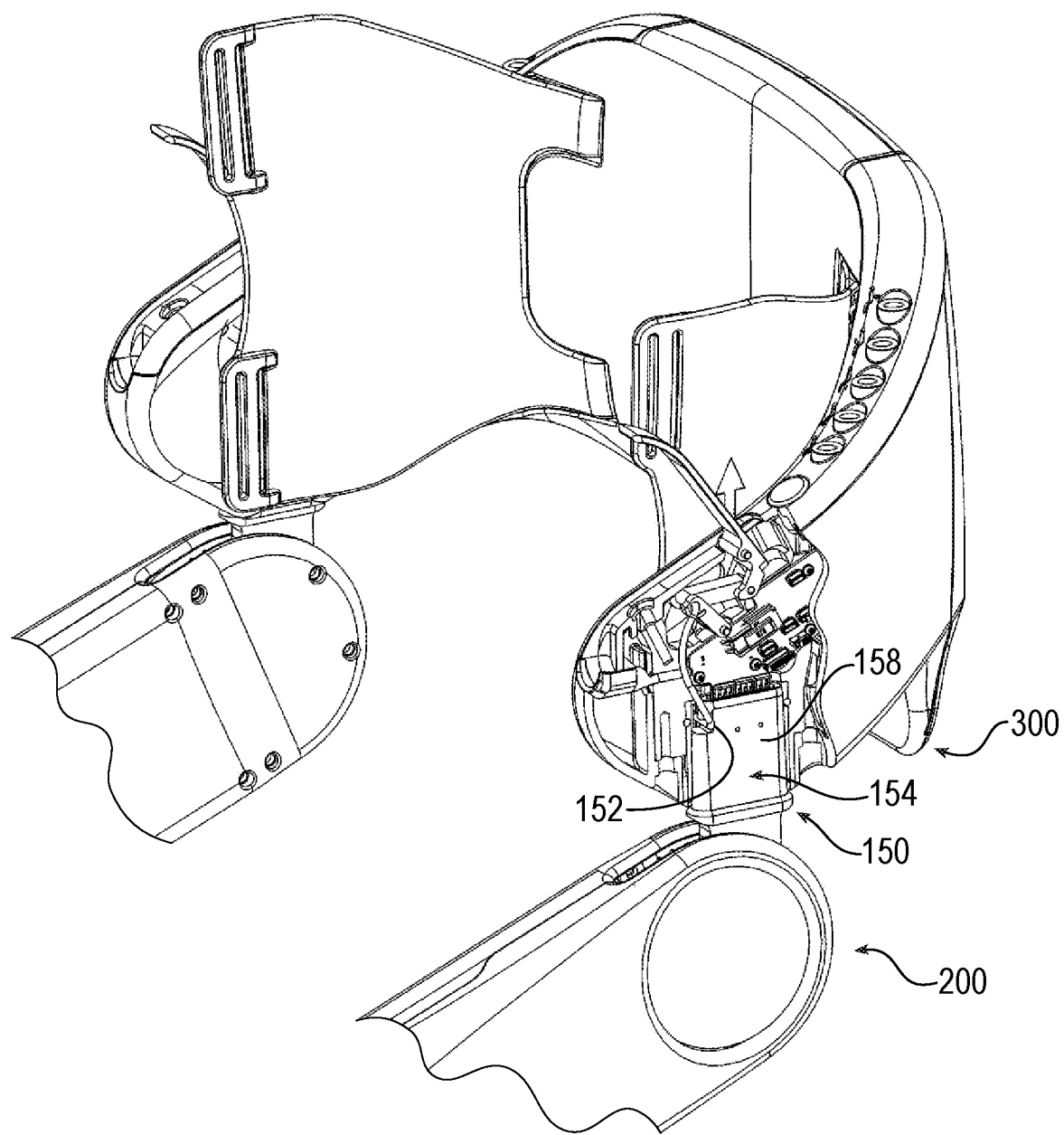
FIG. 7 shows a broken detail view of a portion of an exemplary wearable robotic device having a self-aligning, self-drawing coupler at the hip joint.

Referring specifically to FIGS. 7-13, shown is an exemplary self-aligning, self-drawing coupler for use in a wearable robotic device. In particular, FIG. 7 shows a portion of the hip assembly 300 broken away in order to show the interior workings of the coupler.

A thigh assembly 200 for attachment to a thigh of a user includes a first portion 154 of the self-aligning, self-drawing coupler 150, and a hip assembly 300 for attachment to a hip region of the user has a second portion or receptacle 156 of the self-aligning, self-drawing coupler 150. Although illustrated as a coupler between a thigh and a hip assembly, such coupler may be used at any appropriate connection point of a wearable robotic device.

The coupler 150 may include a latch 152 configured to draw the first portion 154 of the self-aligning, self-drawing coupler to a latched position relative to the second portion 156 of the self-aligning, self-drawing coupler.

The first portion 154 of the self-aligning, self-drawing coupler includes a tapered male portion 158 receivable in a complimentary tapered female portion 160 of the second portion of the self-aligning, self-drawing coupler. These complimentary tapered portions create a self-aligning feature that assists a user when donning a wearable robotic device. For example, as long as the tapered positions are brought into general alignment, the shape of the pieces will cause the pieces to self-align when drawn together.

The length of both the tapered male portion and tapered female portion is preferably longer than a widest width portion. Further, the taper may be in both a width and a depth direction along the length of the portions. Preferably the taper includes a taper angle of between approximately 1 and 10 degrees. One embodiment may include a friction reducing surface, such as Teflon, on at least a portion of the interfacing surface between the male and female portions.

Figure 8:
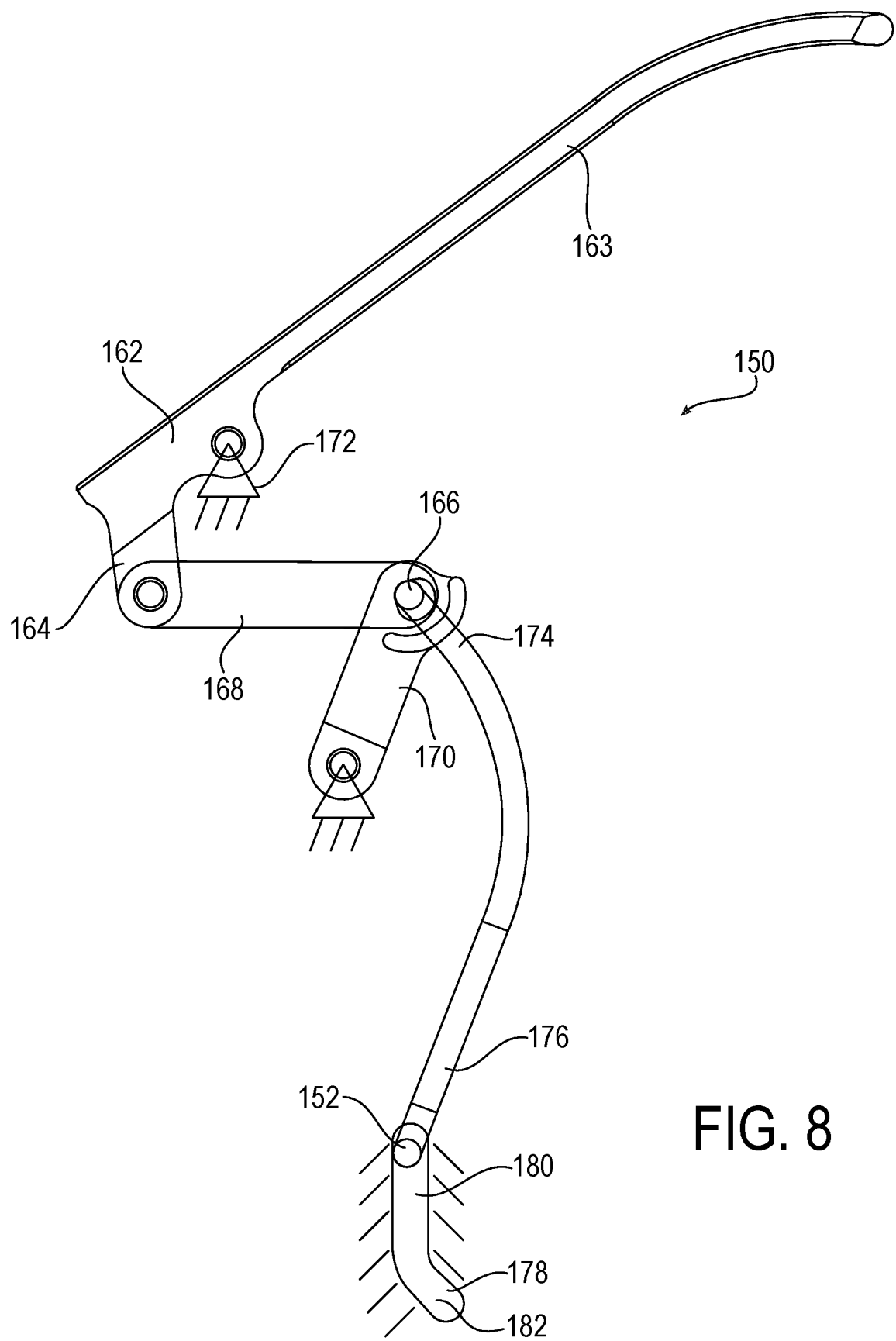
FIG. 8 shows a simplified view of the linkage mechanism of the self-aligning, self-drawing coupler.

As shown in simplified form in FIG. 8, an exemplary coupler 150 may include a four bar linkage including an input link 162, a floating link 168, an output link 170, and a ground link 172 to aid in connecting the two separate components of a wearable robotic device. It may include a manually operable (i.e. operable without tools) lever 163 as the input link 162 with a cantilever portion 164 connecting to the floating link 168.

At the revolute link 166 between the floating link 168 and the output link 170, a sliding latch element 152 is attached at a first end 174. The latch element 152 may be resilient. The other end 176 of the sliding latch element may be restricted to sliding in a guideway or channel 178 for controlling motion of the latch element during operation.

The guideway 178 may include a generally straight draw portion 180 aligned with the female portion of the coupler, and an engagement portion 182 extending laterally away from the draw portion for guiding the latch element into and out of engagement with a corresponding latch element 190 of the second portion 154 of the coupler.

Figure 12:
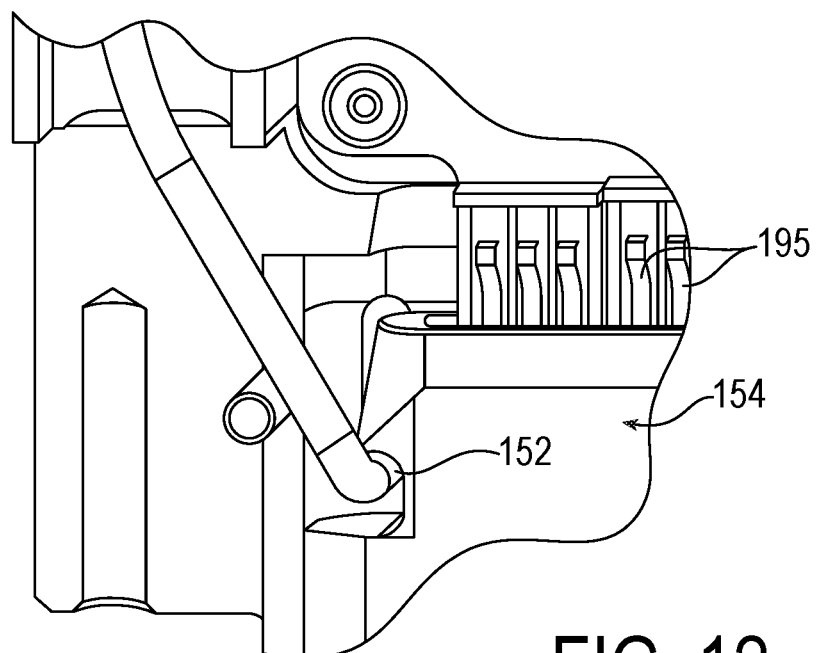
FIG. 12 shows a detail view of the self-aligning, self-drawing coupler at the hip joint with the coupler latch mechanism in a closing position.
Figure 13:
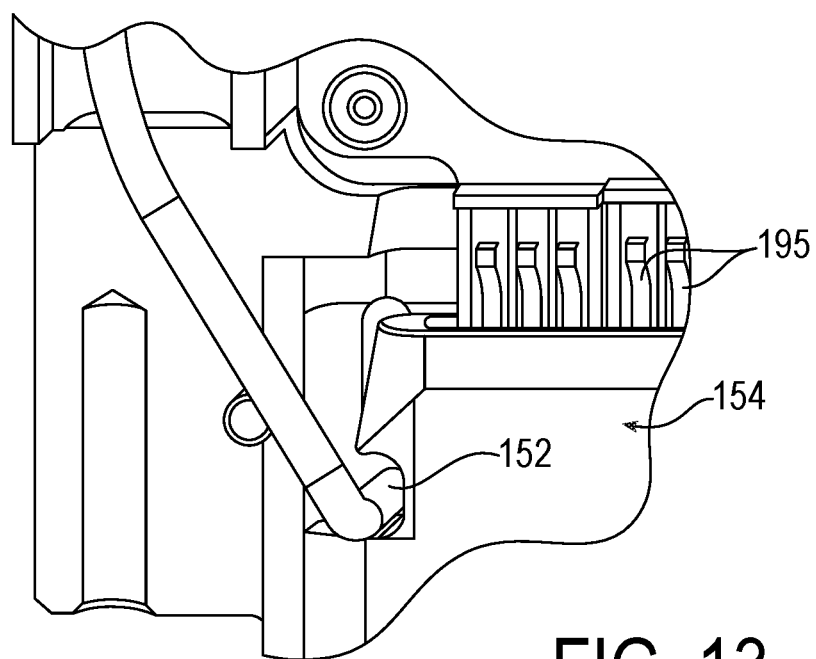
FIG. 13 shows a detail view of the self-aligning, self-drawing coupler at the hip joint with the coupler latch mechanism in an opening position.
Figure 14:
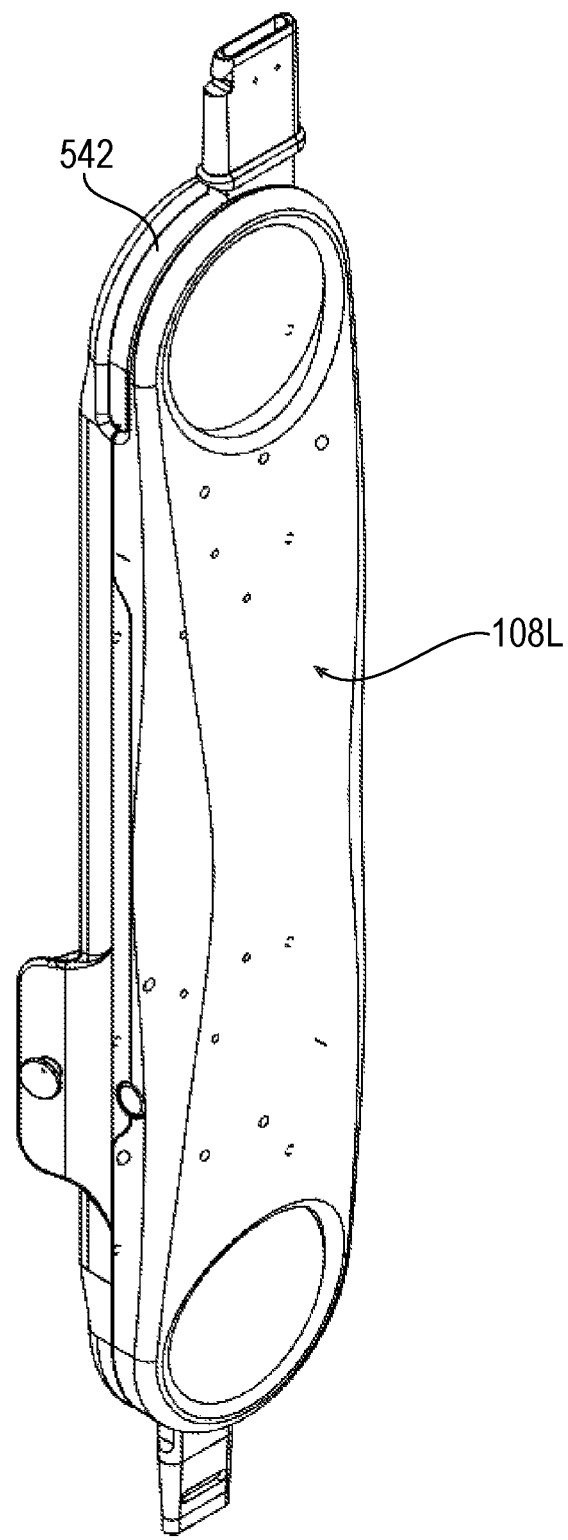
FIG. 14 shows a perspective view of an exemplary thigh assembly having two exemplary actuator cassettes installed therein.
Figure 15:
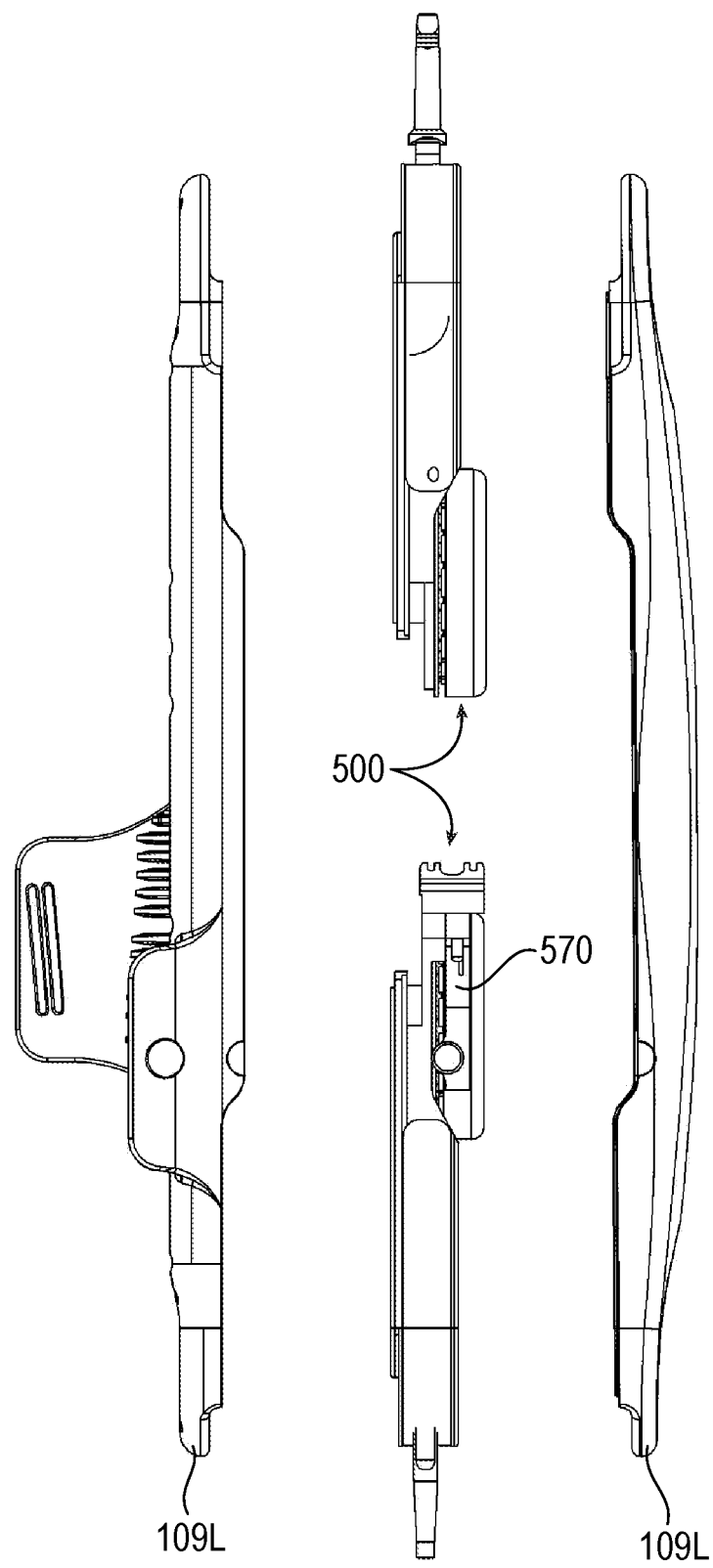
FIG. 15 shows a front exploded view of the exemplary thigh assembly having two exemplary actuator cassettes installed therein.
Figure 16:
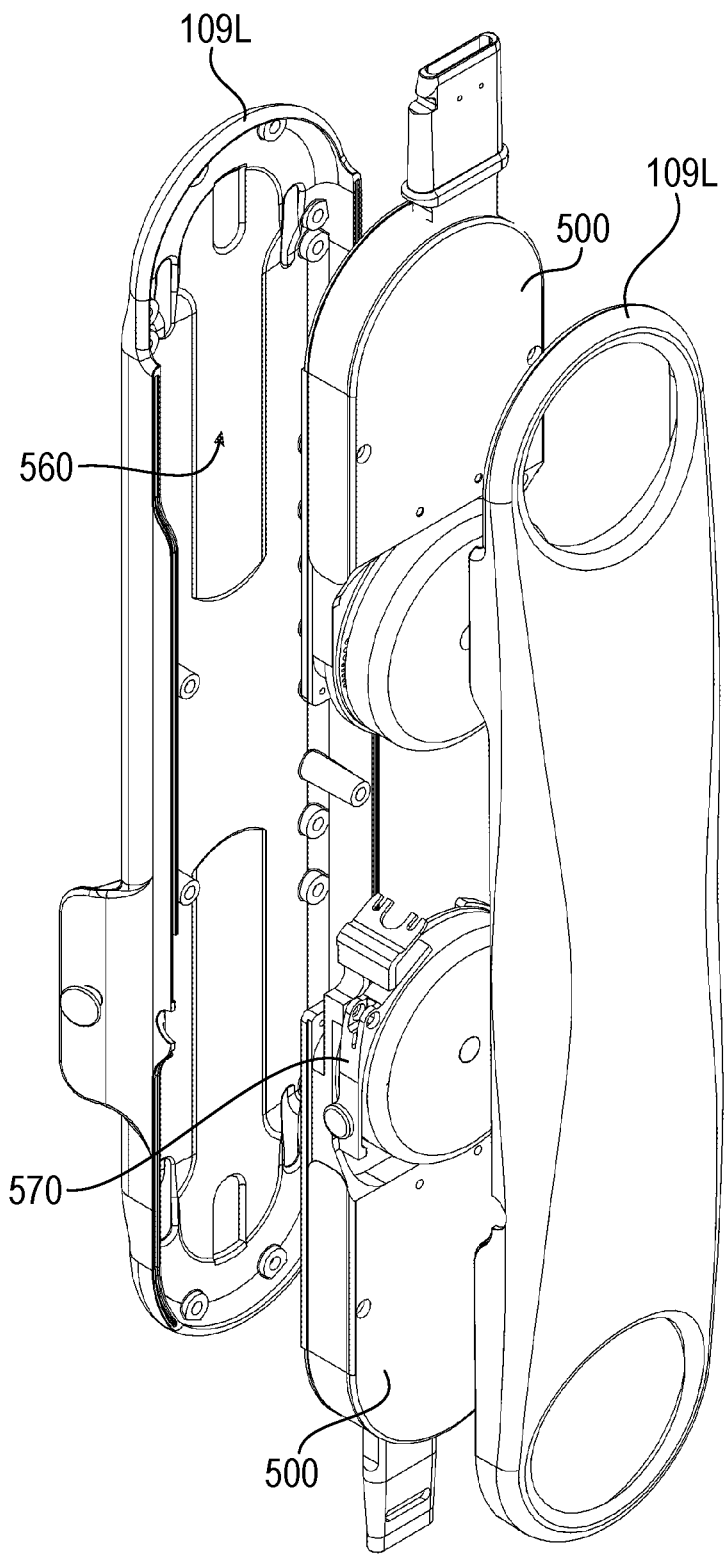
FIG. 16 shows a perspective exploded view of the exemplary thigh assembly having two exemplary actuator cassettes installed therein.
Figure 17:
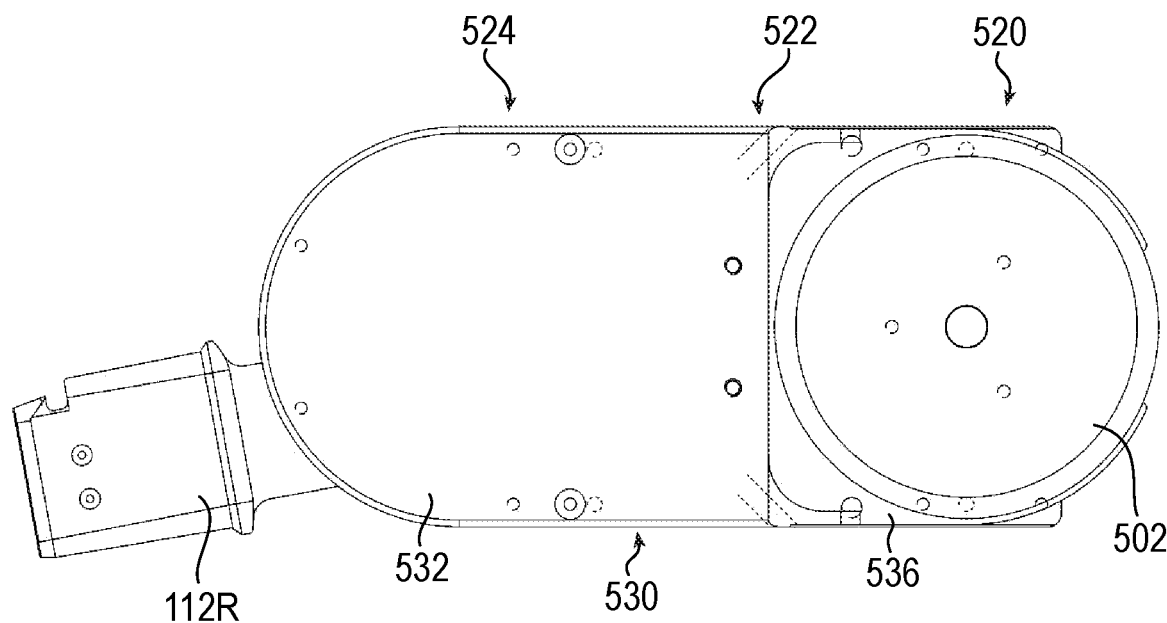
FIG. 17 shows a top view of an exemplary actuator cassette.
Figure 18:
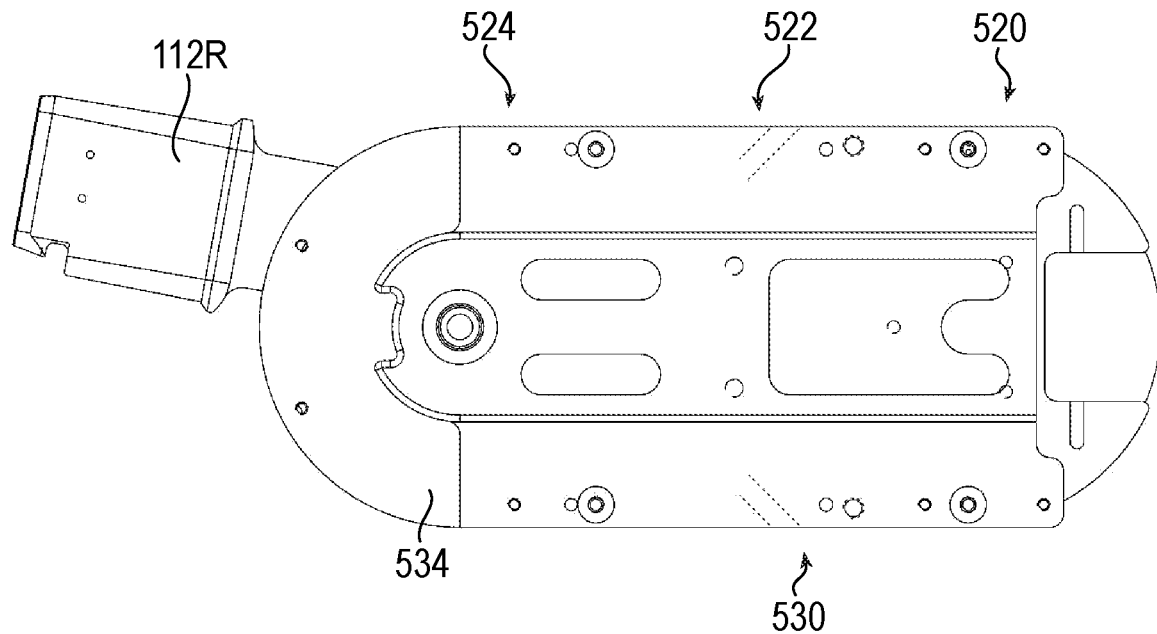
FIG. 18 shows a bottom view of an exemplary actuator cassette.

The guideway the sliding latch element is contained to be within allows the sliding latch element to move in either direction based on the position and direction of the input lever. This movement allows the latch mechanism to draw the connecting link into the receptacle or to eject the link from the receptacle, as shown in FIGS. 12 and 13, respectively. Preferably, the sliding latch element rides in a channel that is curved to push the sliding latch element out of the way in the fully open position allowing for unobstructed removal or insertion.

Figure 9:
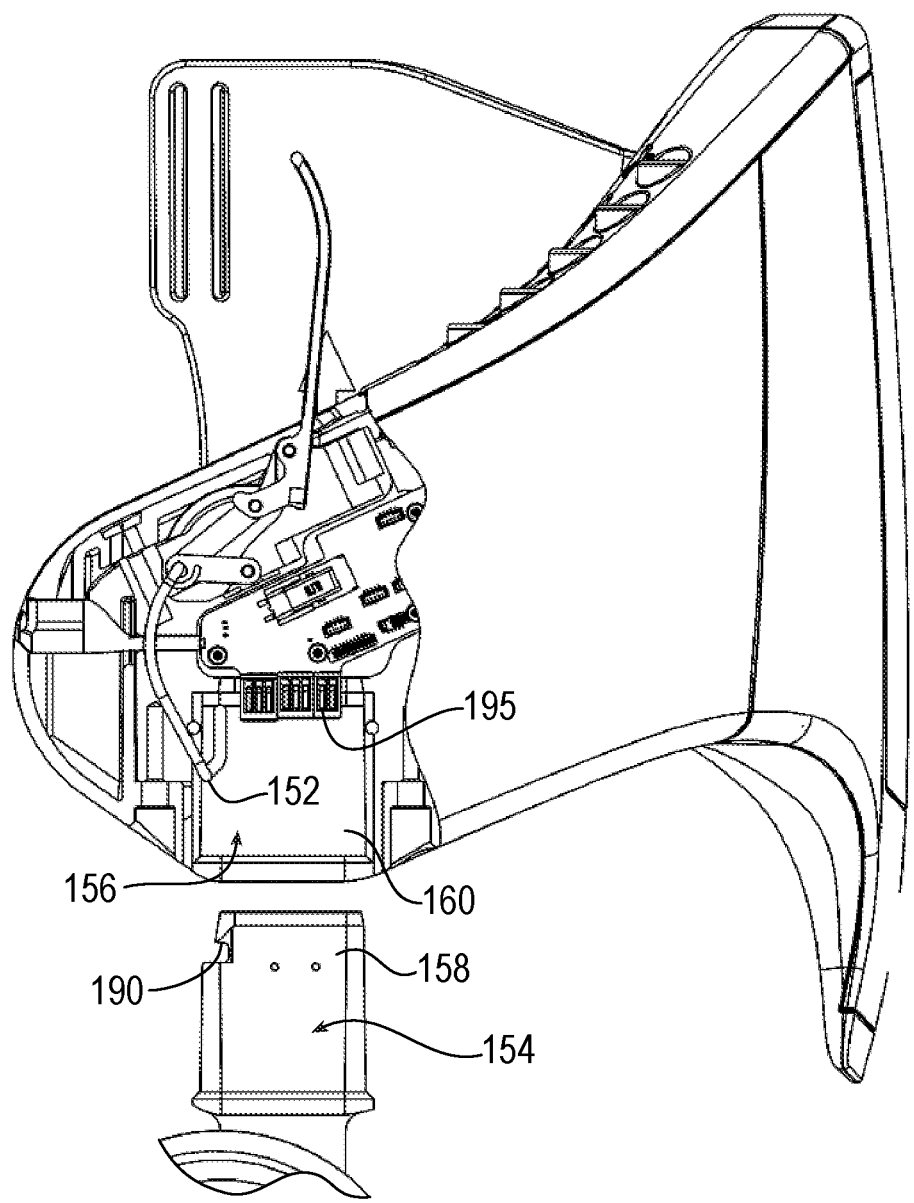
FIG. 9 shows a broken detail view of a portion of the exemplary wearable robotic device having a self-aligning, self-drawing coupler at the hip joint with the coupler latch mechanism in a locked open position.
Figure 10:
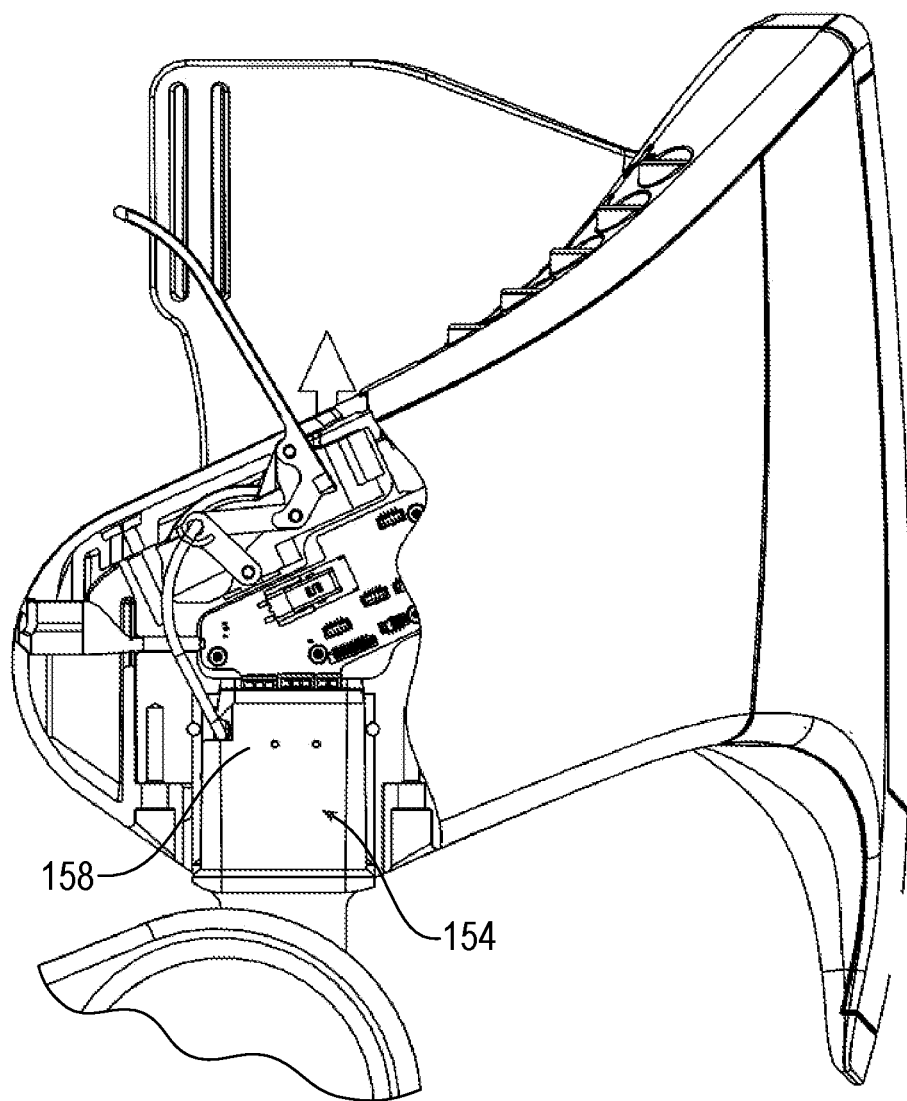
FIG. 10 shows a broken detail view of a portion of the exemplary wearable robotic device having a self-aligning, self-drawing coupler at the hip joint with the coupler latch mechanism in a closing position.
Figure 11:
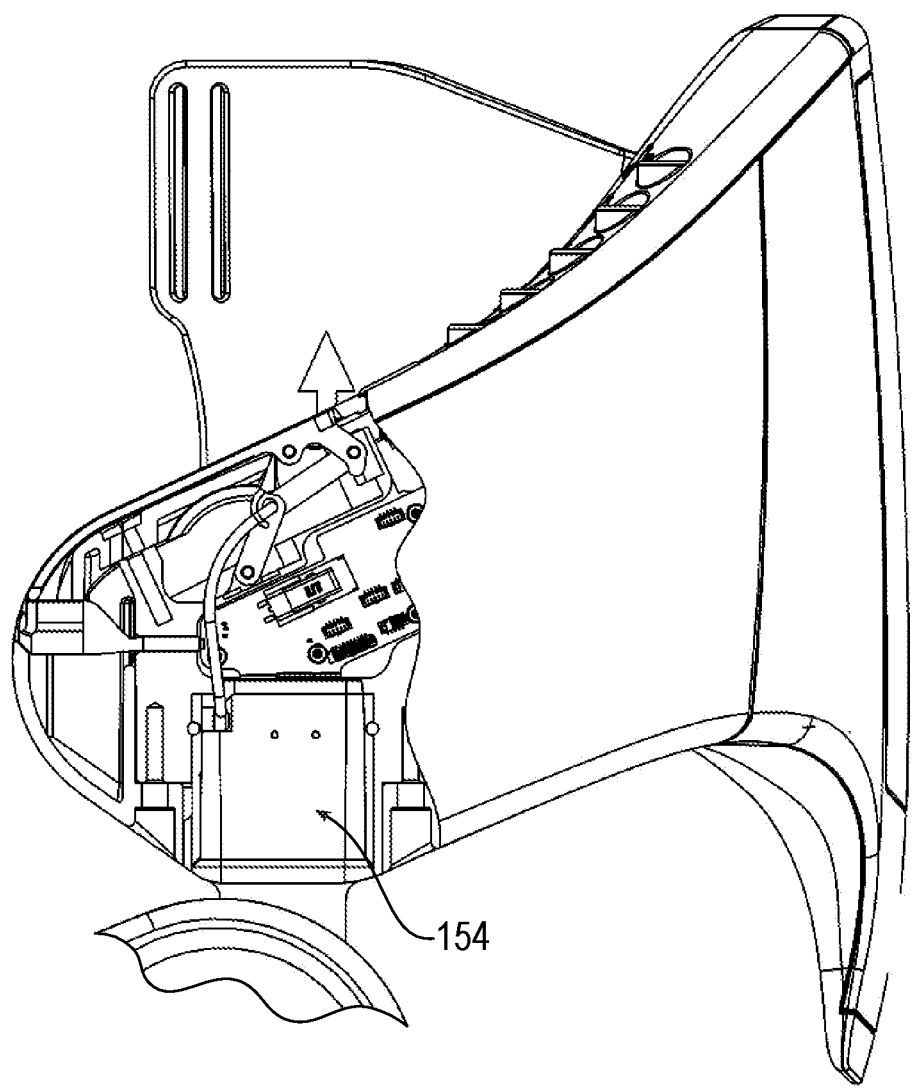
FIG. 11 shows a broken detail view of a portion of the exemplary wearable robotic device having a self-aligning, self-drawing coupler at the hip joint with the coupler latch mechanism in a locked close position.

The resilient latch element 152 may provide a biasing force in the linkage mechanism for locking the linkage mechanism in an over-center configuration. The over-center position may be either in a locked open position as illustrated in FIG. 9, or a locked close position as illustrated in FIG. 11, although, preferably, it is both. The resilient latch, when in an over-center, locked close position, holds the input lever closed with the spring load and takes up tolerance in the hip link. The resilient latch, when in an over-center, locked close position, can secure the lever in an open position and secure the sliding latch element in a position that prevents the sliding latch element from blocking the connecting link during insertion. When the connecting link is inserted, it will catch the sliding latch element 152. With the connecting link partially inserted, the input lever of the four bar linkage can be used to fully insert the connecting link, creating a self-drawing feature.

The male portion of the coupler may include a notch 190 that the sliding latch element can interface with and pull or push the connecting link. This controlled action provides a consistent connection of the link.

In one embodiment the sliding latch element and notch can be used to "key" the connecting link to prevent improper insertion. This also prevents incorrect electrical connections.

As noted above, the connectors 112R, 112L, 114R, and 114L, and/or the self-aligning, self-drawing coupler 150 can be configured to provide mechanical and electrical connections. In the event that an electrical connection is needed between the thigh assembly 108R and lower leg assembly 106R, wires can be routed through the interior of connector 112R to electrical contacts. A corresponding set of electrical contacts 190 would also be provided in the interior of the female portion. Accordingly, when a male portion is locked into the female portion, the electrical contacts are placed in contact with the corresponding electrical contacts within the female portion. A similar configuration can be provided for links 112L, 114R, and 114L. It is noted though that the various embodiments self-aligning, self-drawing coupler may be used on any suitable device and may, in particular, be used with any other exemplary devices disclosed herein.

Actuator Cassette

In the various embodiments, in order to maintain a low weight for orthosis and a reduced profile for the various components, a substantially planar drive system is used to drive the hip and knee articulations. For example, each motor can respectively drive an associated joint through a speed-reduction transmission using an arrangement of sprocket gears and chains substantially parallel to the plane of sagittal motion.

The powered joints may be implemented by disposing a joint sprocket gear 504 at one end of thigh assembly housing 109R parallel to the sagittal plane and configuring the joint sprocket gear 504 to rotate parallel to the sagittal plane. To provide the sagittal plane torque for knee joint 102R, the connector 112R can extend from the joint sprocket gear 504 and be mechanically connected, so that rotation of the joint sprocket gear 504 results in application of torque to the lower leg assembly 106. A slot or receiving element can be provided for the connector 112R to link the thigh assembly 108R and lower leg assembly 106R. The receiving element and the connector 112R can be configured such that the connector can removably connect the thigh assembly 108R and lower leg assembly 106R. In the various embodiments, clips, screws, or any other types of fastener arrangements can be used to provide a permanent or a removable connection. In some embodiments, quick connect or "snap-in" devices can be provided for providing the connection. That is, these quick connect devices allow connections to be made without the need of tools. These types of quick connect devices can not only be used for mechanically coupling, but for electrical coupling. In some embodiments, a single quick connect device can be used to provide both electrical and mechanical coupling. However, the various embodiments are not limited in this regard and separate quick connect devices can be provided for the electrical and mechanical coupling. It is worth noting that with quick disconnect devices at each joint, the orthosis can be easily separated into three or five modular components—right thigh, left thigh, right lower leg, left lower leg, and hip assemblies—for ease of donning and doffing and also for increased portability.

The knee joint 104R may be actuated via operation of a motor 502, as discussed above. The motor 502 can be an electric motor that drives the knee joint 104R (i.e., joint sprocket gear 504) using a two-stage chain drive transmission. For example, as shown in FIG. 20, a first stage can consist of the motor 502 driving, either directly or via a first chain, a first drive sprocket gear 514. The first drive sprocket gear 514 is mechanically coupled to a second drive sprocket gear 516 so that they rotate together about the same axis based on the power applied by motor 502 to first drive sprocket gear 514. The second drive sprocket gear 516 can be arranged so that it is disposed in the same plane as the joint gear 504. Thus, a second chain can then be used to drive joint sprocket gear 504 using the second drive sprocket gear 516 and actuate the knee joint 104R. The gear ratios for the various components described above can be selected based on a needed amount of torque for a joint, power constraints, and space constraints.

Each stage of the chain drive transmission can include tensioners, which can remove slack from a chain and mitigate shock loading. Such tensioners can be adjustable or spring loaded.

In addition, a brake 570 can be provided for motor 502. For example, a solenoid brake may be provided which engages a brake pad against the rotor 524 of the motor 502 in one state, and disengages the brake pad in another state. However, the various embodiments are not limited to this particular brake arrangement and any other methods for providing a brake for motor 502 can be used without limitation.

The configuration illustrated in FIG. 20 has been discussed above with respect to an arrangement of sprocket gears and chains. However, the various embodiments are not limited in this regard. That is, any other arrangement of gears, with or without chains, and providing a reduced profile can be used. Further, the various embodiments disclosed herein are not limited to an arrangement of gears and/or chains. For example, in some configurations, a belt and pulley arrangement could be used in place of the chain and sprocket arrangement. Further, a friction drive arrangement can also be used. Also, any combination of the arrangements discussed above can be used as well. Additionally, different joints can employ different arrangements.

In the various embodiments, a motor for each of joints 102R, 102L, 104R, 104L can be configured to provide a baseline amount of continuous torque and a higher amount of torque for shorter periods of time. For example, in one configuration, at least 10 Nm of continuous torque and at least 25 Nm of torque for shorter (i.e., 2-sec) durations are provided. In another example, up to 12 Nm of continuous torque and 40 Nm of torque for shorter (i.e., 2-sec) durations. As a safety measure, both knee joints 104R and 104L can include normally locked brakes, as discussed above, in order to preclude knee buckling in the event of a power failure.

Referring now to FIGS. 14-20, consolidating the moveable parts described above into self-contained units, referred to herein as "cassettes," allow for ease of maintenance and replacement because cassettes are swappable, making them easier to service or requiring less of a variety in spare components. As used herein, "self-contained" means that the cassette includes everything necessary to operate in a fully functional manner if supplied with power. Thus, for example, if power is supplied to electrical contacts of the cassette, the cassette would actuate.

In the illustrated embodiment, the motor is integrated onto a common baseplate along with sprockets that control the motion of a joint link. Bearings and chains, with and/or without tensioners provide smooth and efficient transfer of motion from the motor to the joint angle. Integrating the motor into the cassette allows for a thinner overall package configuration and provides consistent alignment among parts. Moreover, integrating the motor also creates a larger surface area to transfer and emit heat generated by the motor.

In the instance of a mobility assistance device, as in the current invention, these cassettes may pertain to a specific joint or set of joints on the device. Each may have a unique actuation unit or share an actuation unit. They may include actuators, with or without a power source, and/or a method of transmitting movement. The illustrated embodiment includes a brushless DC motor with chains and sprockets to create and transmit motion, however other embodiments may utilize electric motors, linear actuators, piezoelectric actuators, belts, ball screws, harmonic drive, gear drive (bevel or planetary), or any combination thereof. One embodiment may also house electronics and/or sensors.

The self-contained unit(s) can be preassembled to aid in manufacturing the broader device. This allows for quick servicing of the device since individual cassettes can be swapped out and serviced.

Therefore, a removable, self-contained, ovular actuator cassette 500 may be receivable in a receptacle of a wearable robotic device. The cassette 500 may include a first circular portion 520 housing a motive device (e.g., an electric motor) 502. A second circular portion 522 may be longitudinally offset and longitudinally overlapping the first circular portion and may house a first portion of a drivetrain 514, 516 operatively coupled to and driven by the motive device 502. A third circular portion 524 may be longitudinally offset from the first and second circular portions and longitudinally overlapping the second circular portion and may house a second portion of the drivetrain 504.

These three overlapping circular portions make an ovular shape. Therefore, an ovular housing 530 may support the motive device 502 and drivetrain 502, 514, 516. Long sides of the ovular housing are straight and parallel with each other and tangentially terminate as curved end surfaces of the ovular housing.

An output 112R may protrude from and be rotatable with respect to the housing and driven by the drivetrain.

The housing may include a top plate 532 on which the motive device is mounted. As shown in FIG. 20, the drive shaft of the motive device 502 may protrude through the top plate 532.

The housing may also include a bottom plate 534 coupled to the top plate 532. The drive train is sandwiched between and supported by the top plate 532 and the bottom plate 534. Preferably, the motive device 502 is mounted outside the top and bottom plates on a laterally offset portion 536 of the top plate.

As shown in the figures, the maximum depth of the cassette measured along a rotational axis of the motive device is less than the maximum width and the maximum length of the cassette, thereby achieving a thin, flat profile.

The output 112R may protrude through an output opening 540. Slide covers 542 disposed in the output opening and movable with the output 112R to cover portions of the output opening not occupied by the output may also be provided. Alternatively, brushed covers or other means known in the art may be used to protect the interior of the cassette from contamination.

As discussed above, the output 112R may be the first portion of the self-aligning, self-drawing coupler discussed above.

The cassette may be disposed in an appropriate receptacle 560 of the thigh assembly.

Retention System

A wearable robotic device often needs to be donned and doffed under difficult circumstances, including, for example, by a user who is paralyzed. Therefore, an improved attachment system is desirable.

A body assembly, for example, a hip assembly, may include an attachment device 600, 600' for attaching to the first portion of the user's body. The attachment device may include a tensioning system 650, 650' for retention of the first body assembly to the user's body. In preferred embodiments, the tensioning system includes both a tensionable member 652, 652' and a tensioning member 654, 654'.

Figure 21:
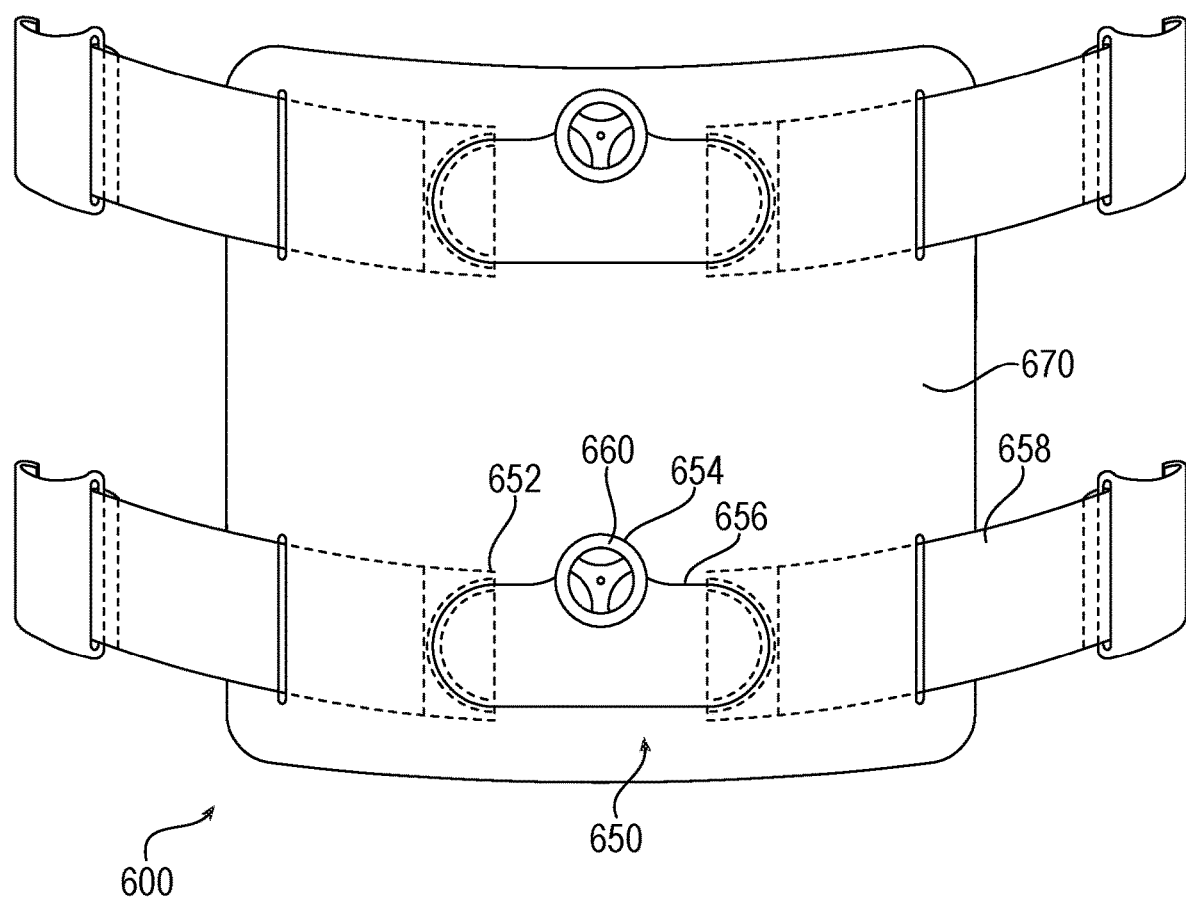
FIG. 21 shows an exemplary attachment device for use in an exemplary hip assembly having a retention system with a tensionable member and a tensioning member.
Figure 22:
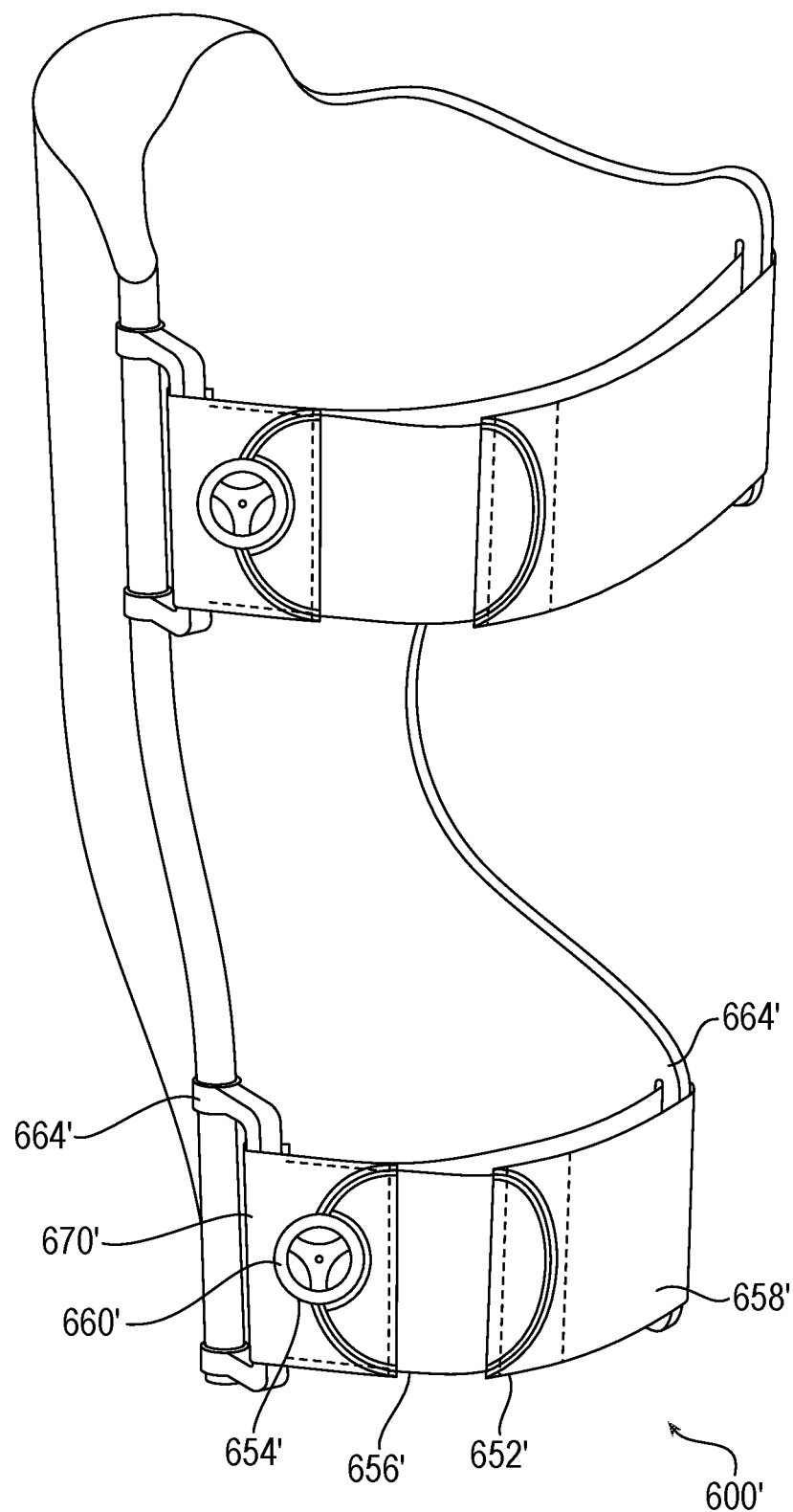
FIG. 22 shows an exemplary attachment device for use in an exemplary lower leg assembly having a retention system with a tensionable member and a tensioning member.
Figure 23:
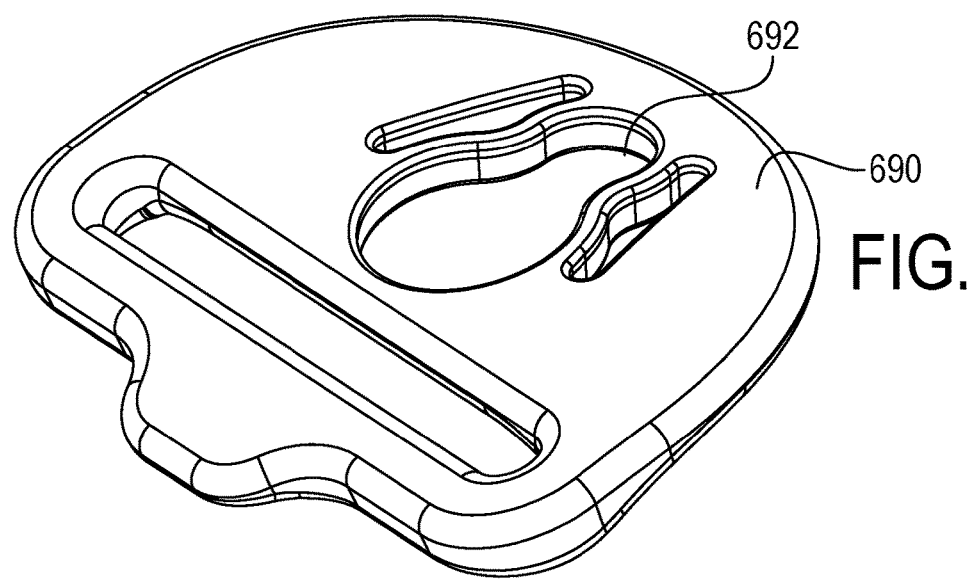
FIG. 23 shows a perspective view of an exemplary buckle for use in an exemplary attachment device.
Figure 24:
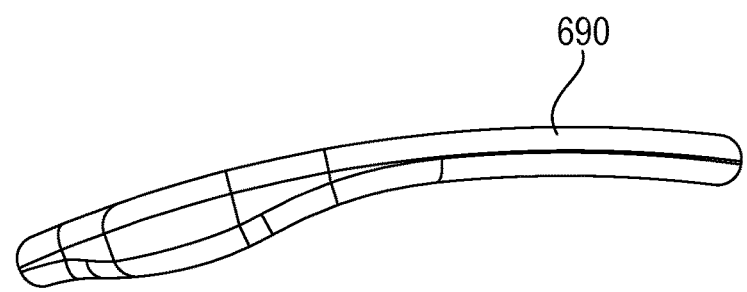
FIG. 24 shows a side view of the exemplary buckle for use in an exemplary attachment device.
Figure 25:
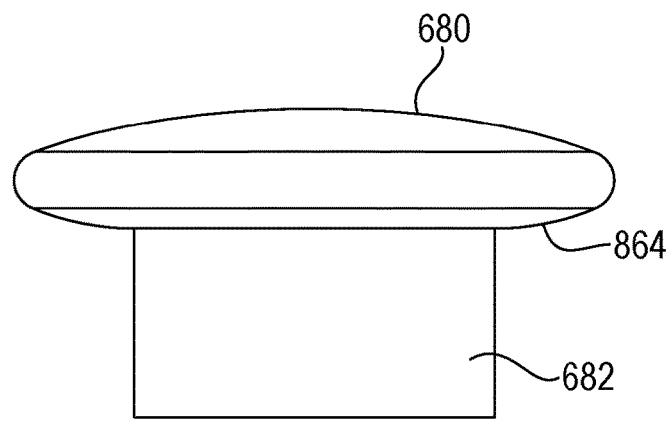
FIG. 25 shows an exemplary button and post for use in an exemplary clip of an exemplary attachment device.
Figure 26:
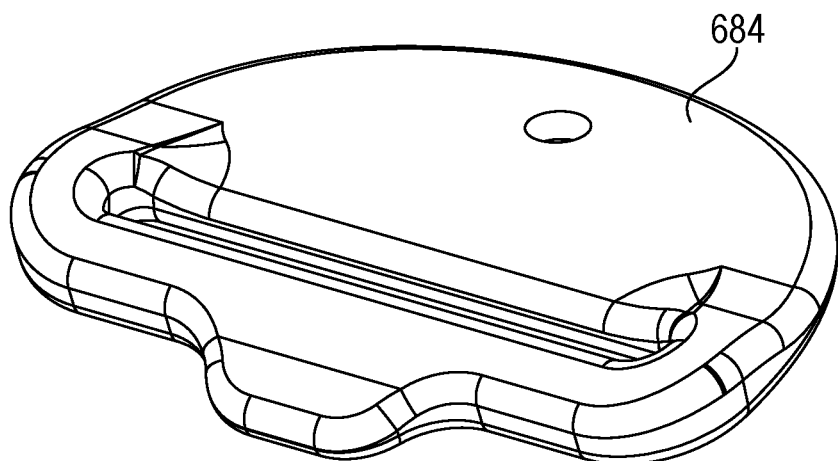
FIG. 26 shows an exemplary clip without an attached button.
Figure 27:
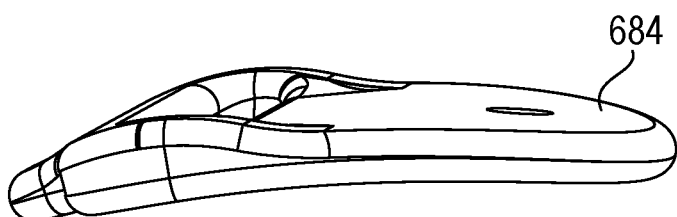
FIG. 27 shows another view of the exemplary clip without an attached button.

As shown in FIGS. 21 and 22, a cable or lace 656, 656' is threaded through a looped strap 658, 658' and connected back onto itself.

The tensioning system preferably includes a cable reel system having a cable reel 660, 660' and a cable 656, 656' extending from the reel, and cable guides (not shown). The reel may be a spring-loaded rotating spool that winds or unwinds the cable to either tension or untension the cable. Suitable devices to use for the reel are cable reel devices available under the name BOA from Boa Technology, Inc. of Denver, Colo., and described in U.S. Pat. Nos. 7,954,204 and 7,992,261, incorporated by reference in their entireties. The reel may be mounted to the substrate 670, 670', as by use of plastic rivets, and the like.

Preferably, the cable reel is a rotating spool that winds or unwinds the cable and, preferably includes a toothed housing configured for receiving the ends of the cable, each end rotationally linked to a spool contained within the housing of the cable reel. A knob having a spring-loaded assembly cooperates with the housing and the spool for manually winding the cable around the spool. The knob and spring-loaded assembly cooperate to engage the spool with the housing to provide a ratchet feature for winding the spool when the knob is turned in one direction to tension the cable, and for releasing the spool to untension the cable. The cable may be, for example, a nylon coated, stainless steel cable.

The cable reel 660, 660' may be mounted to a plastic support piece (not shown) that retains the housing with or without the need for other retention methods, such as thread, removable brackets, adhesives, etc.

At the furthest extent, the strap does not extend beyond the plastic support base. The preferred embodiment utilizes the support base as a low friction surface for the strap to slide against and provides a larger surface area for the lace to distribute pressure. When the spool retracts the lace the strap is effectively shortened as it is pulled toward the spool at the base of the support. This shortening tightens the strap when it is attached at one end and the support is attached at another, completing a loop.

As shown in FIG. 22, the tail of the strap 658' may be is attached to a rigid structure of the body assembly at attachment anchor 664, 664'. The attachment could be permanent or temporary. A preferred method would be temporary, allowing for the entire strap to be adjusted or removed. Some methods for attachment could include threading it back on itself, hook and loop fasteners, button fasteners, or any combination of the above or other fastening method. Exemplary embodiments thread the strap 658' through a series of slots to create adequate friction that secures the strap. This method allows the strap to be adjusted to accommodate a wide range of overall lengths.

In exemplary embodiments, the strap may be composed of or contain hook or loop material that can be used to secure the strap to the frame at an attachment anchor 664' or to attach other accessories, such as padding.

As shown in FIG. 21, the attachment device may include a sleeve to contain the support, lace, and strap.

Padding may be placed on the back side of the support 670. This could be adhered to the support, to the sleeve (if present) or floating in place. The padding aids further in the comfort and distribution of pressure.

Figure 28:
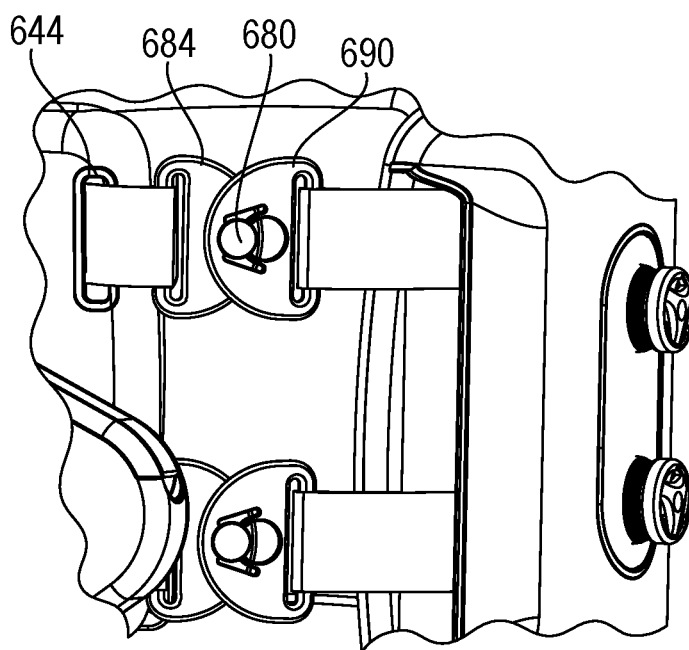
FIG. 28 shows an exemplary attachment device for use in an exemplary hip assembly having a retention system with a tensionable member and a tensioning member.
Figure 29:
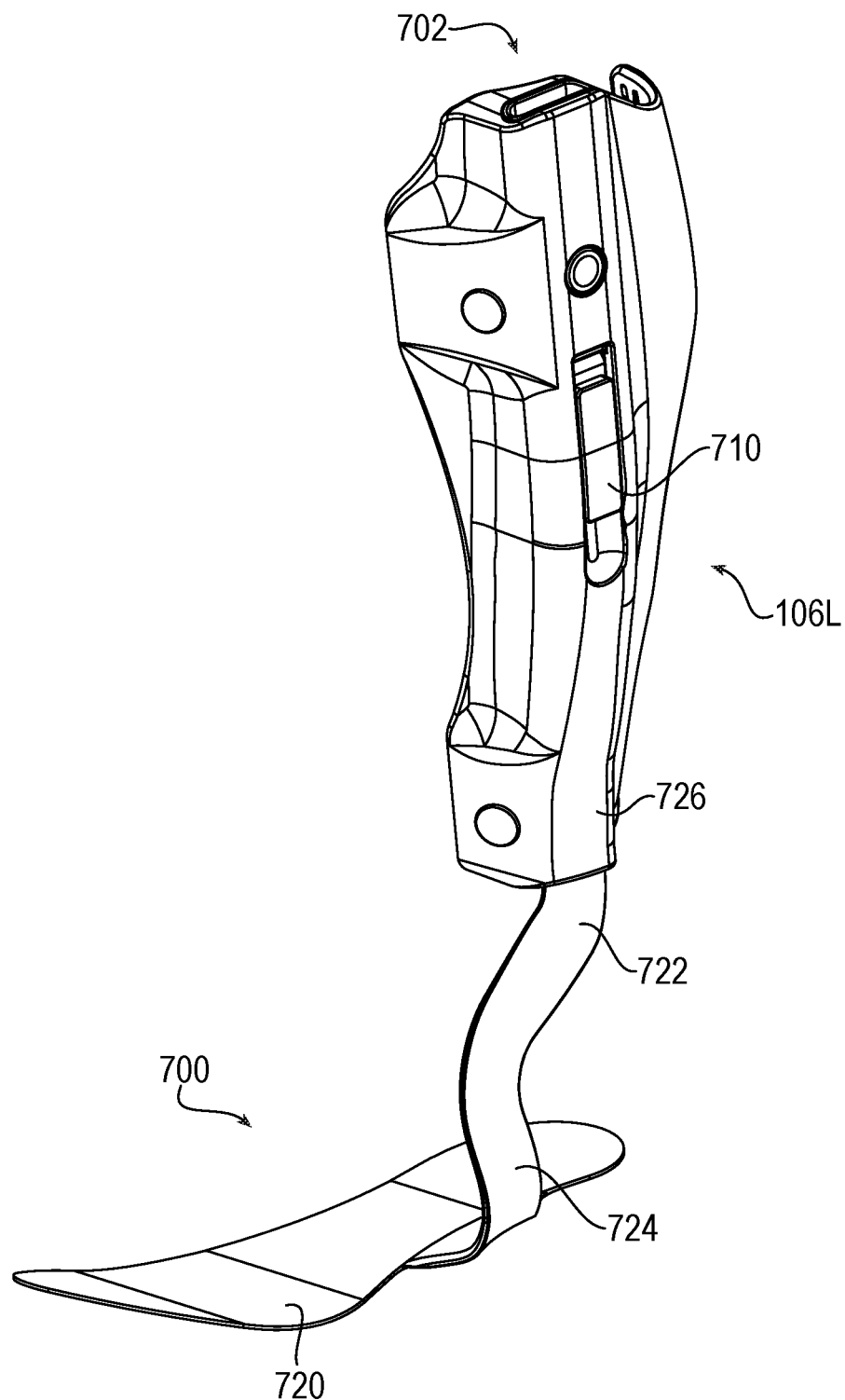
FIG. 29 shows an exemplary lower leg assembly having an exemplary integrated ankle-foot orthotic.

As shown in FIG. 28, a mechanism for attaching the support to the frame may include a quick connect/disconnect. A preferred embodiment includes a button hole and post design, as detailed in FIGS. 23-27. On either the frame or the strap support 684 is a button 680 atop a post 682 and a buckle/clip 690 with a keyhole opening 692. Preferably, the keyhole includes a first circular opening overlapping a second, larger circular opening, the larger circular opening disposed distal the first, smaller opening in relation to the button 680. The keyhole structure allows for the buckle to slide over the larger diameter of the button head and slide tight around the post.

One embodiment may include both the button/post and keyhole features to be secured to straps; when they are connected they join the two.

The present invention discloses a round post that allows the buckle to revolve. Further, the bottom portion of the button head 684, just above the connection to the post is slightly curved. This curvature allows the clip 690 to pivot. The degree of pivot is dependent on the height of the post in relation to the thickness of the buckle and the curvature of the bottom of the button relative to the diameter of the post.

The button hole and post connect/disconnect method can be use independently of the tensioning strap method to secure other strapping to a frame or another strap. This buckle and clip design can be used independently or combined with other strapping methods.

As disclosed above, the adjustable and removable straps allow for coarse adjustment of the attachment device, while tensioning by the cable reel allows for fine adjustment of the attachment device.

AFO System

The lower-leg assembly 106L, 106R may include an ankle foot orthotic (AFO) 700 that can be used independently or attach to a joint, such as one found on a wearable robotic device. Preferred embodiments include a quick connect/disconnect 702 between the lower-leg assembly and the rest of the robotic system so that, for example, the lower leg assembly could be worn all day, and the rest of the wearable robotic assembly could be attached when required. This can result in much quicker and easier donning and doffing, as a dedicated AFO would not have to be removed from under a shoe and replaced by an AFO integrated into a wearable robotic device.

Figure 30:
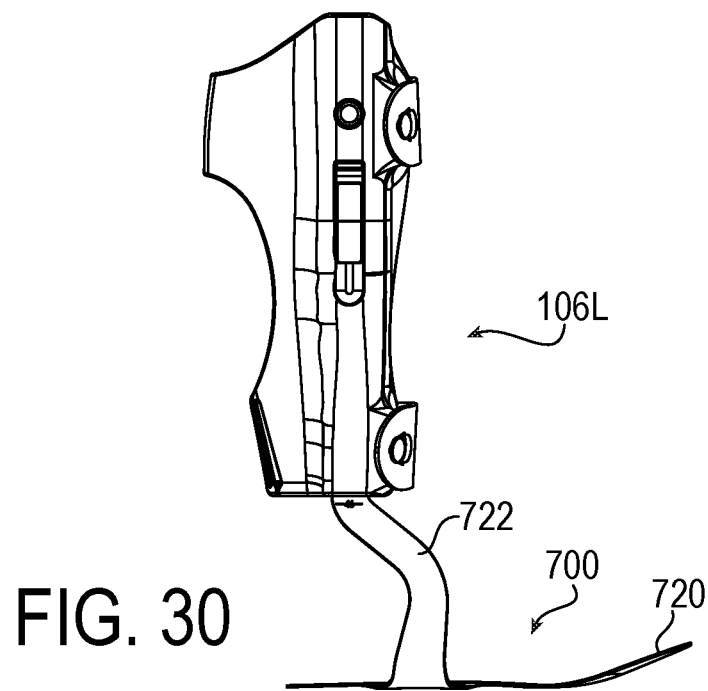
FIG. 30 shows another view or the exemplary lower leg assembly having an exemplary integrated adjustable ankle-foot orthotic with the orthotic retracted.
Figure 31:
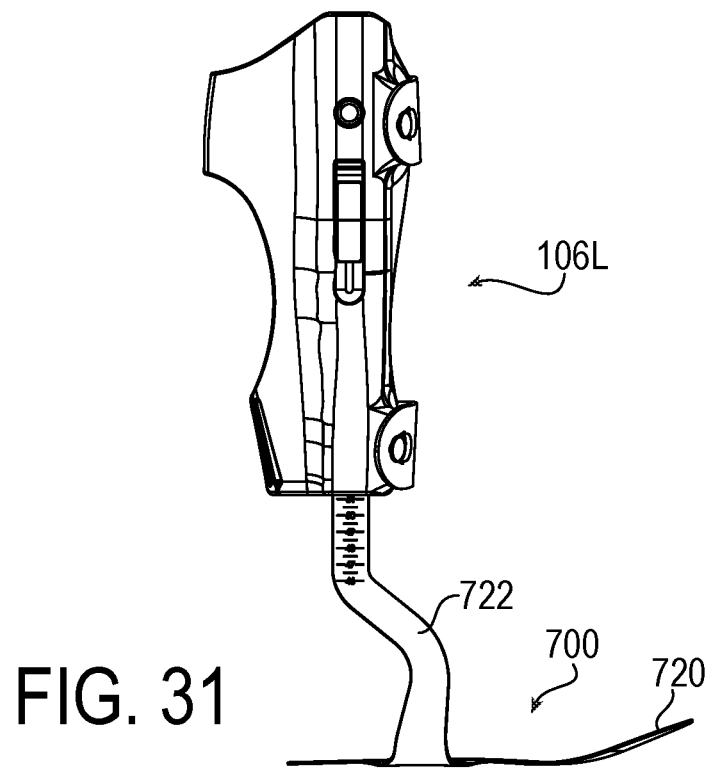
FIG. 31 shows another view of the exemplary lower leg assembly having an exemplary integrated adjustable ankle-foot orthotic with the orthotic partially extended.

Further, as shown in FIGS. 30 and 31, exemplary lower-leg assemblies allow for the length to be adjusted while worn by the user or separate from the user. One embodiment may include markings to indicate total assembly length or that can be used to determine said length.

The lower leg assembly 106L includes an AFO having a plantar element 720 which may be of a rigid, thin-sheeted material. This plantar element would be placed under the sole of a user's foot, and may fit within a shoe. A leg element 722 may also be made of rigid thin-sheeted material, and may have a lower portion 724 rigidly connected to and extending upwardly from the plantar element. The lower portion of the leg element and the plantar element are adjustably coupled to the housing 726 of the lower-leg assembly. Although only the lateral side of the illustrated AFO provides load bearing support, other embodiments may bear support at the front, rear, medial, or any combination thereof.

Figure 32:
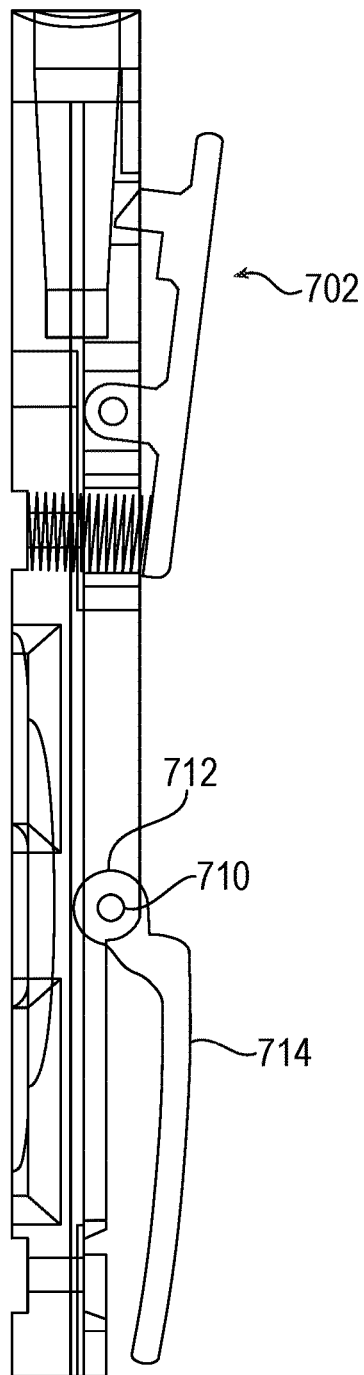
FIG. 32 shows a portion of an exemplary lower-leg assembly having a quick connect coupler at the top end and a cam-lock adjuster at a lower end in a locked position for use with an exemplary ankle-foot orthotic.
Figure 33:
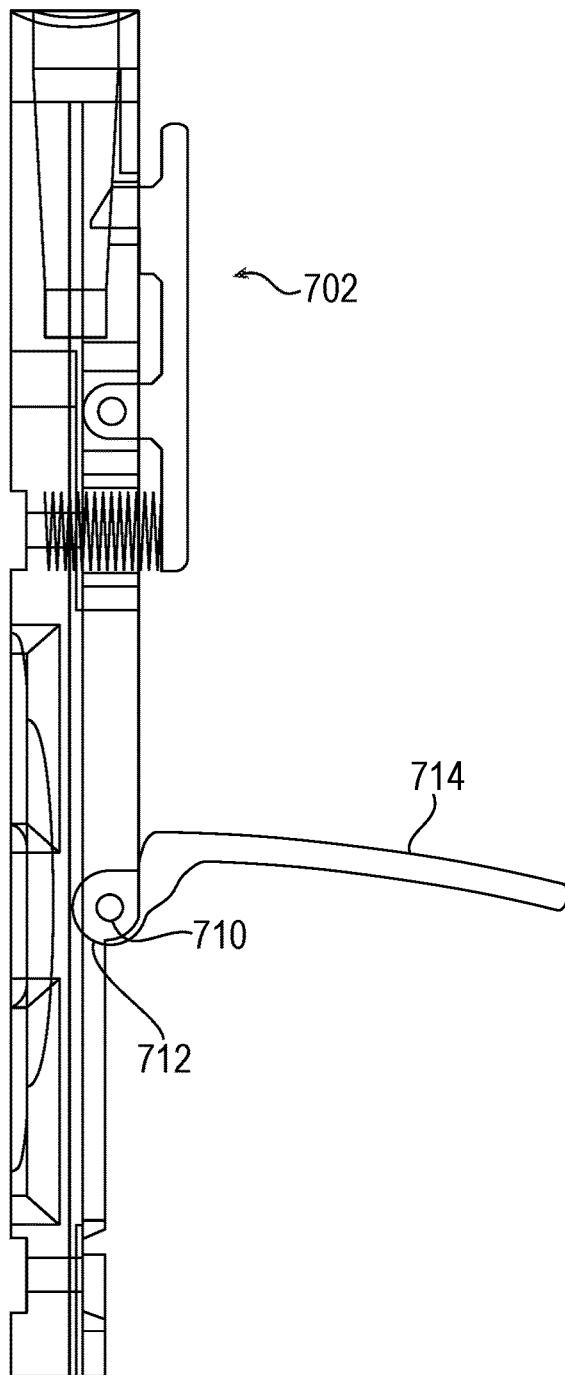
FIG. 33 shows a portion of an exemplary lower-leg assembly having a quick connect coupler at the top end and a cam-lock adjuster at a lower end in an unlocked position for use with an exemplary ankle-foot orthotic.
Figure 34:
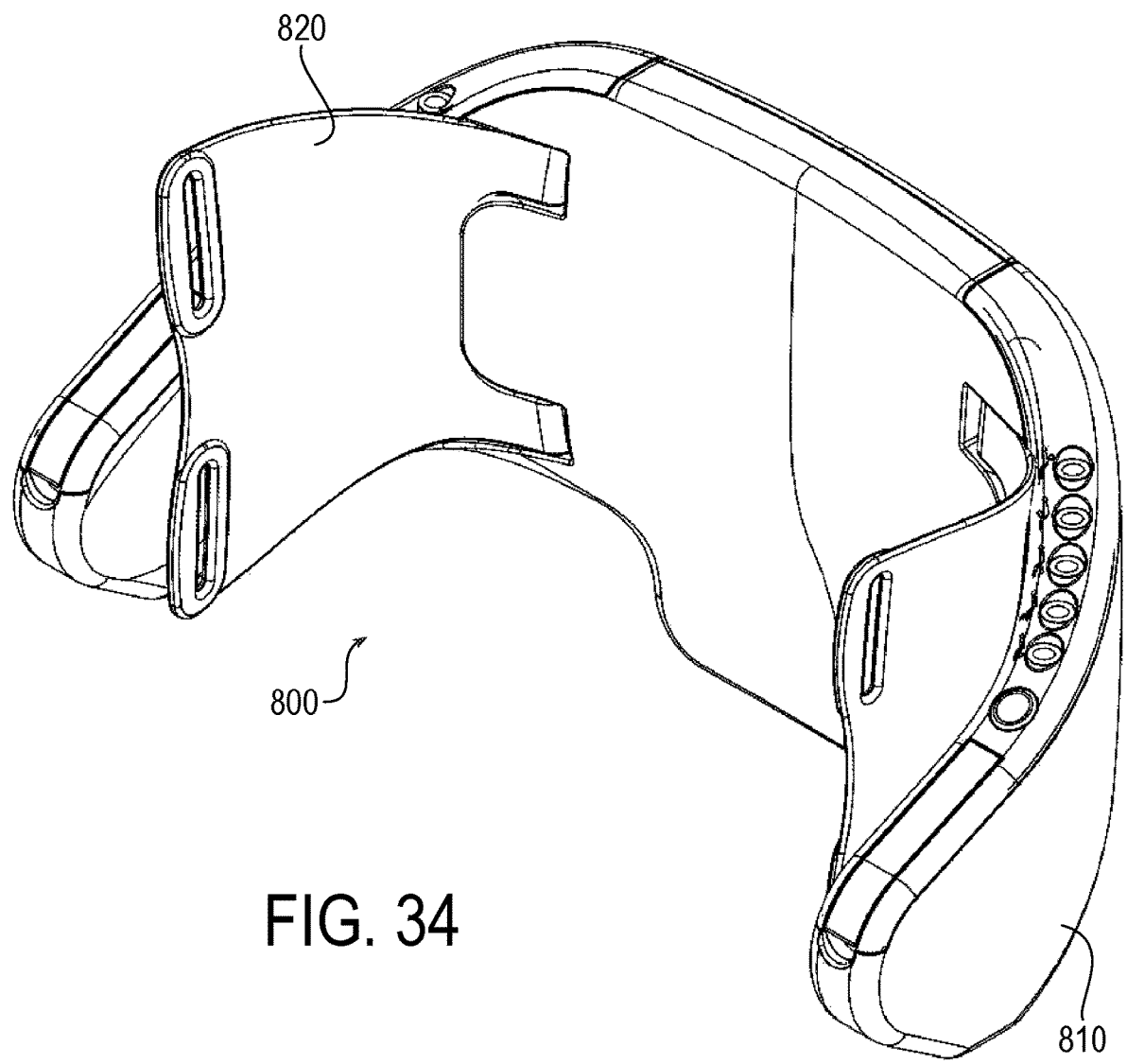
FIG. 34 shows an exemplary hip assembly with a removable hip wing.

Further, exemplary embodiments may include a quick adjust mechanism 710, shown in more detail in FIGS. 32 and 33, utilizing a cam lock 712 device movable by way of a manually operated lever 714 that allows for infinitely variable length between a maximum and a minimum without the use of tools or power source.

Hip Wings

Referring now to FIGS. 34-39, a hip assembly 800 includes pivoting hip wings as part of an attachment device that attaches a portion of a wearable robotic device to a user. Because these wings may be standard sizes or semi-customized or customized to the user customized to a user based on size and/or support needed based on physical limitations of the user, the wings may need to be removed on a regular basis in clinical settings. Therefore, exemplary embodiments include a quick connect/disconnect mechanism that is manually operable (i.e. operable without tools).

An exemplary wearable robotic device includes a hip assembly 800 attachable to a hip region of a user's body and coupled to another body assembly (e.g., a thigh assembly) and rotatable with respect to the first body assembly via a motive device housed in at least one of the first body assembly or the hip assembly. The hip assembly includes a rigid housing 810 and a removable attachment device or hip wing 820 attachable to the hip region of a user's body and removable from the rigid housing by operation of a manually operable removal mechanism 830.

Figure 35:
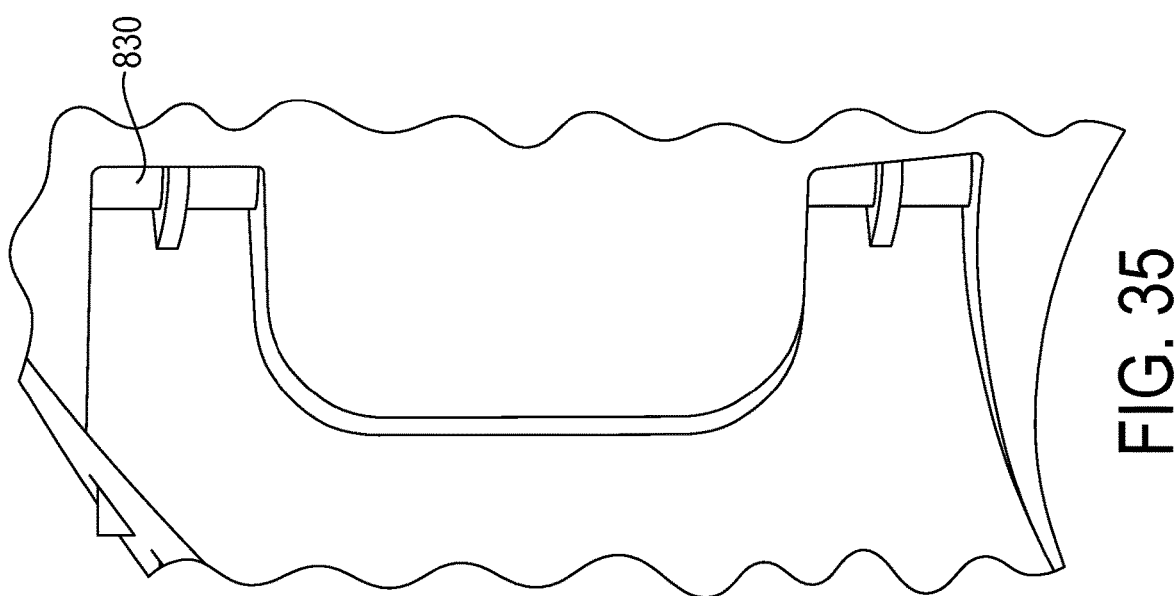
FIG. 35 shows a partial view of the hip assembly with the hip wing removed.
Figure 37:
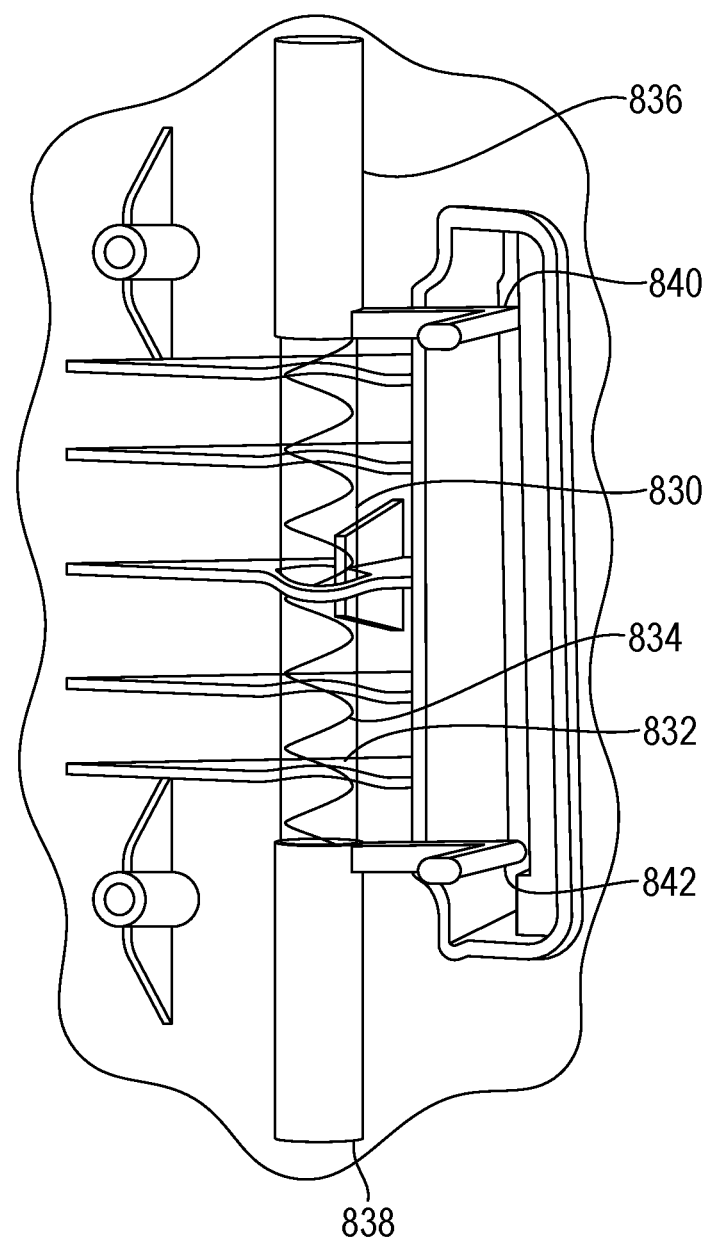
FIG. 37 shows a partial view of the hip assembly with a portion of the housing removed and the guide cylinder invisible to show the spring of the removal mechanism.
Figure 38:
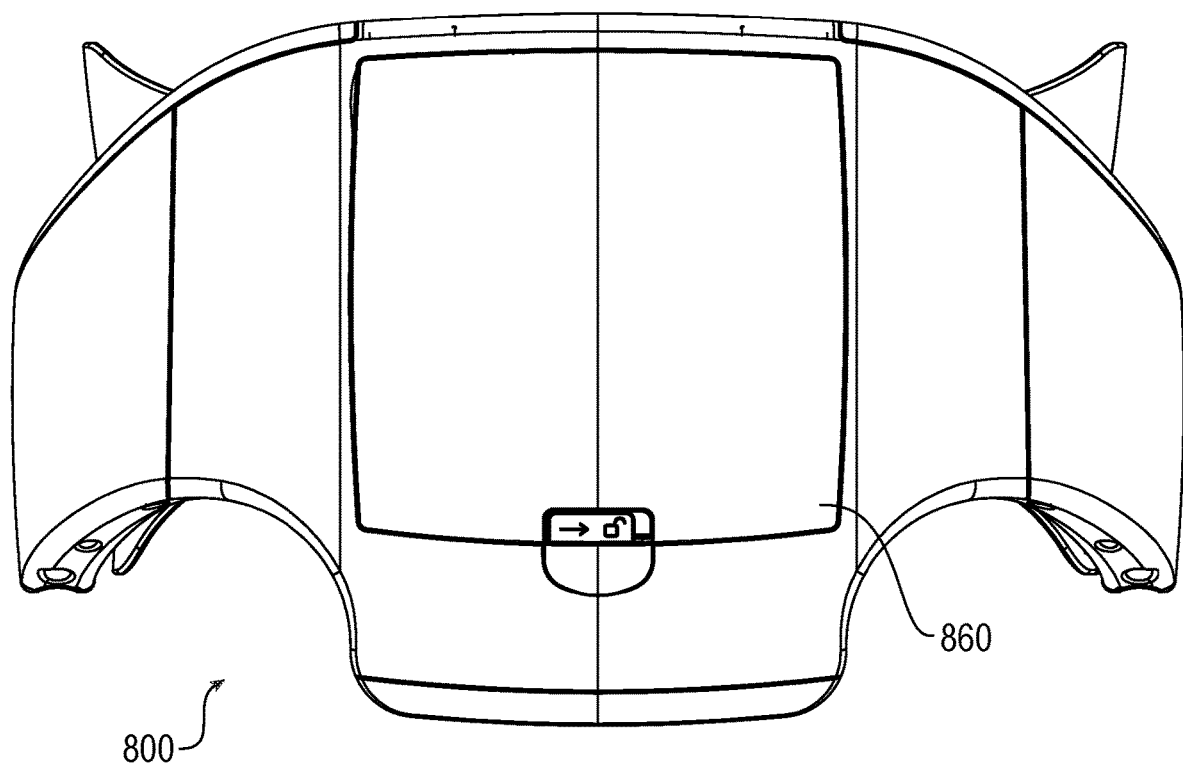
FIG. 38 shows a rear view of the exemplary hip assembly with the battery installed in the batter receptacle.
Figure 39:
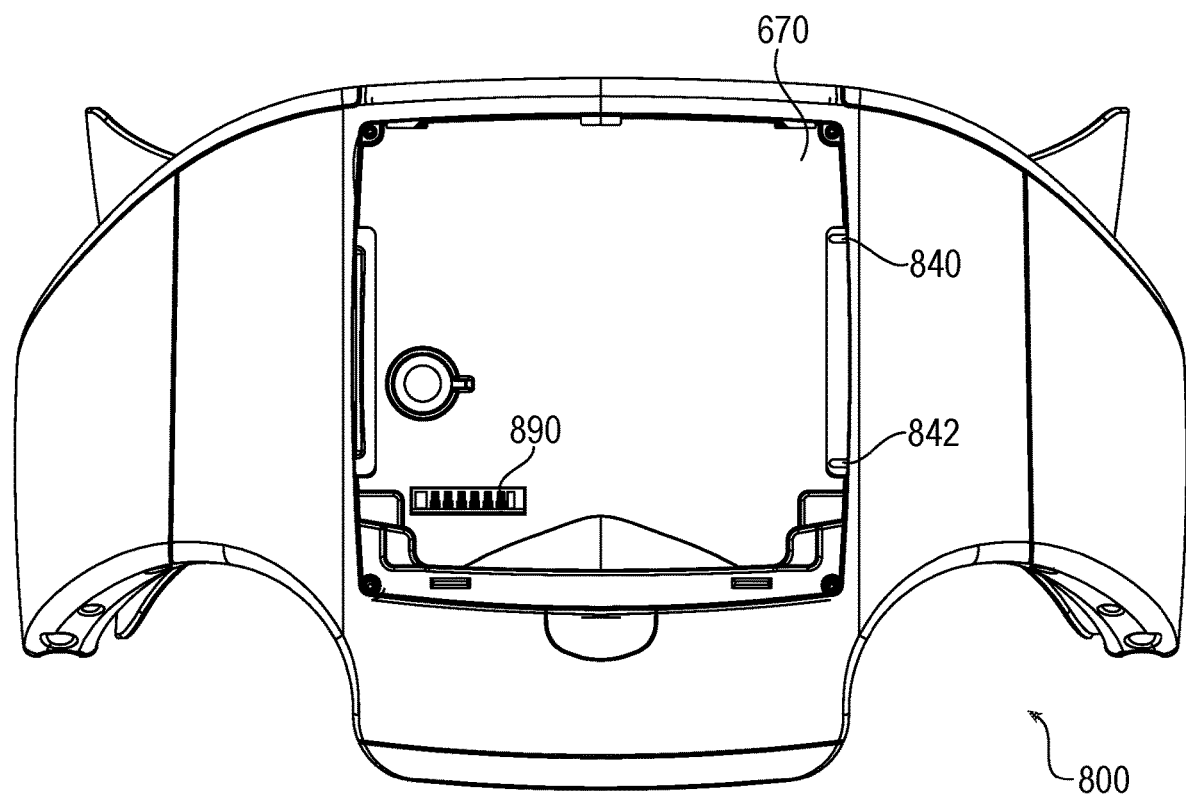
FIG. 39 shows a rear view of the exemplary hip assembly with the battery not installed in the batter receptacle, revealing the removal mechanism of one of the hip wings.
Figure 40:
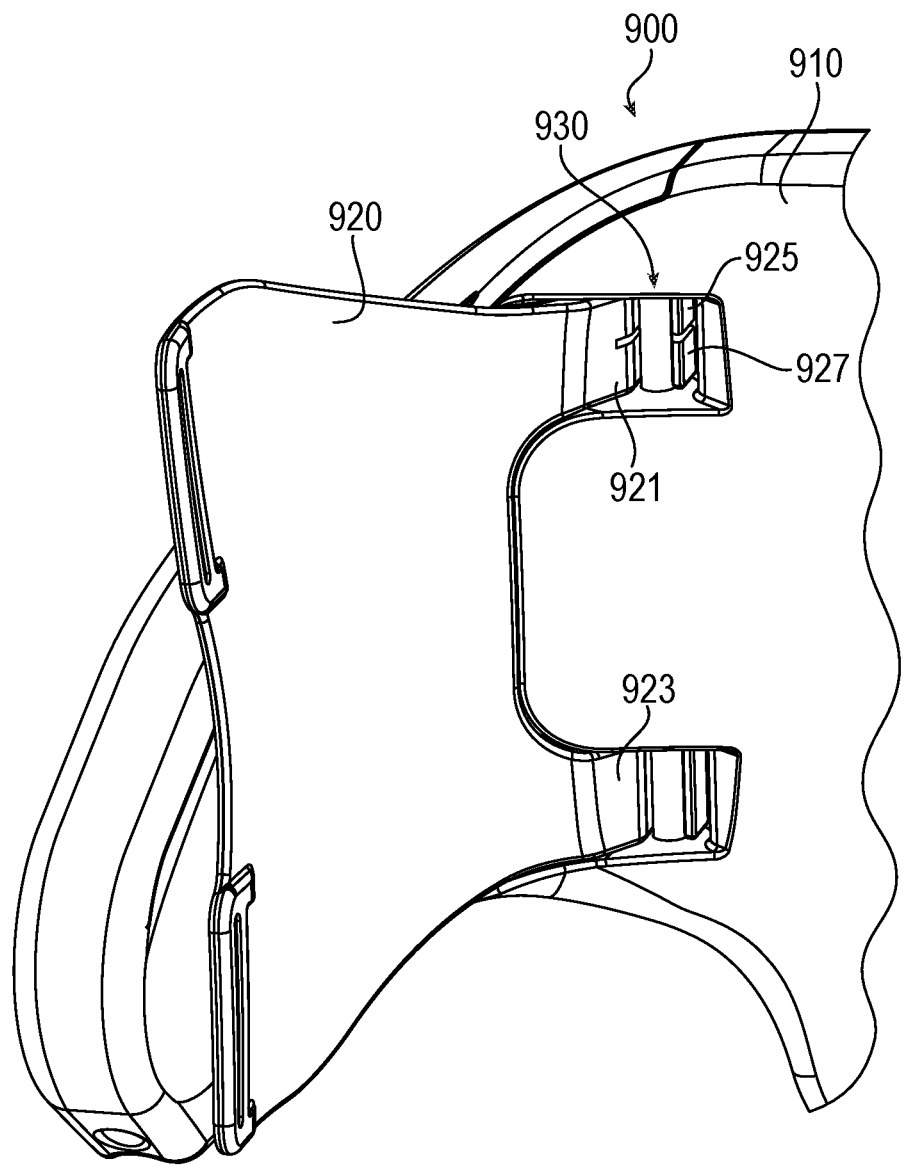
FIG. 40 shows a partial view of the hip assembly with another exemplary attachment mechanism between the hip wing and the rigid housing of the hip assembly.

FIG. 35 shows a detailed view of the hip assembly with the hip wing 820 removed and the removal mechanism 830 visible.

Figure 36:
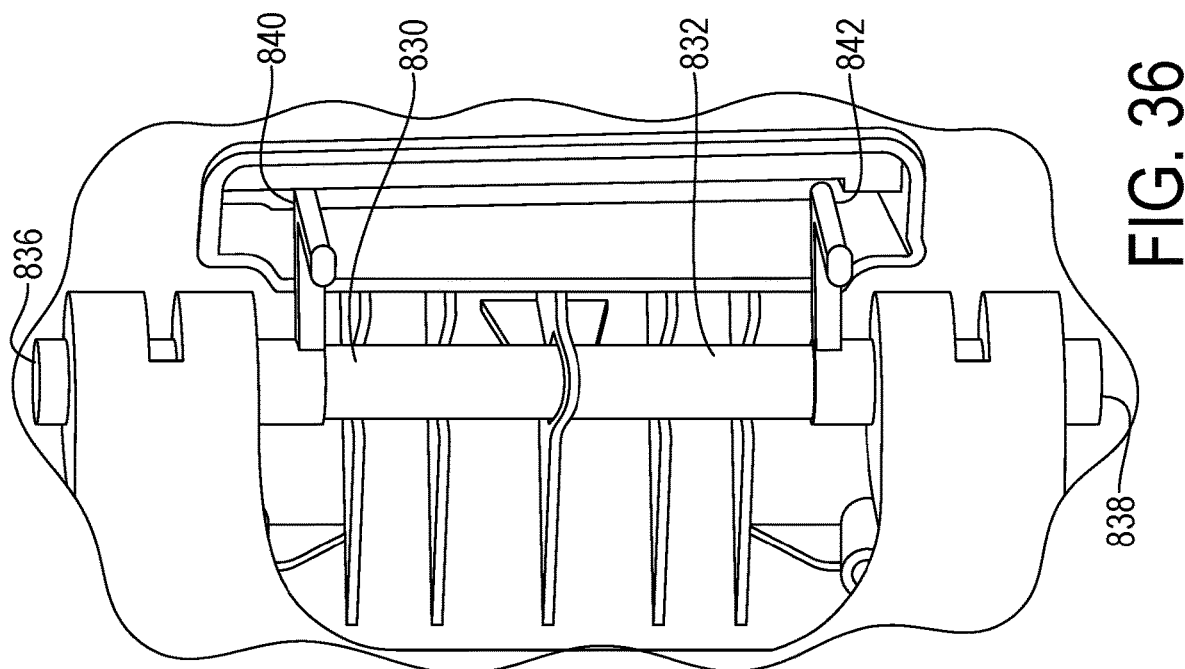
FIG. 36 shows a partial view of the hip assembly with a portion of the housing removed to show the interior of the hip assembly.

FIG. 36 shows another detailed view of the hip assembly, this time with a portion of the rigid housing 810 removed for clarity. As is evident, the removal mechanism may be a quick-release hinge pin.

The removal mechanism 830 includes a central guide cylinder 832 housing a spring 834 longitudinally outwardly biasing first and second finger-operated pins 836, 838 slidably disposed on opposite longitudinal sides of the guide cylinder. These pins or end caps act as hinges when installed with the wings on the rigid housing. When the end caps are pinched together, compressing the spring, the pins retract into the ridged frame, allowing the wings to be freely removed or inserted. The guide cylinder prevents the spring from buckling during compression and may reduce friction to minimize force to activate the latch to release the wings.

In exemplary embodiments the wing release is not exposed during operation. Rather, laterally extending grip portions 840, 842 may protrude into a battery receptacle 870. This way, the wings cannot be removed when the battery 860 is in place because access to the removal mechanism is precluded when the battery is installed in the battery receptacle. Further, the battery may be shaped such that the battery cannot be connected if wings are only partially installed.

The battery receptacle further includes electrical contacts 890 for mating with corresponding electrical contacts of the battery (not shown).

Turning now to FIGS. 40-46, an exemplary embodiment of the hip assembly is shown at 900. The hip assembly 900 is substantially the same as the above-referenced hip assembly 800, and consequently the same reference numerals but indexed by 100 are used to denote structures corresponding to similar structures in the hip assembly. In addition, the foregoing description of the hip assembly 800 is equally applicable to the hip assembly 900 except as noted below. Moreover, it will be appreciated upon reading and understanding the specification that aspects of the hip assemblies may be substituted for one another or used in conjunction with one another where applicable.

The hip assembly includes a rigid housing 910 and a removable attachment device or hip wing 920 attachable to the hip region of a user's body and removable from the rigid housing by operation of a manually operable removal mechanism 930.

Figure 41:
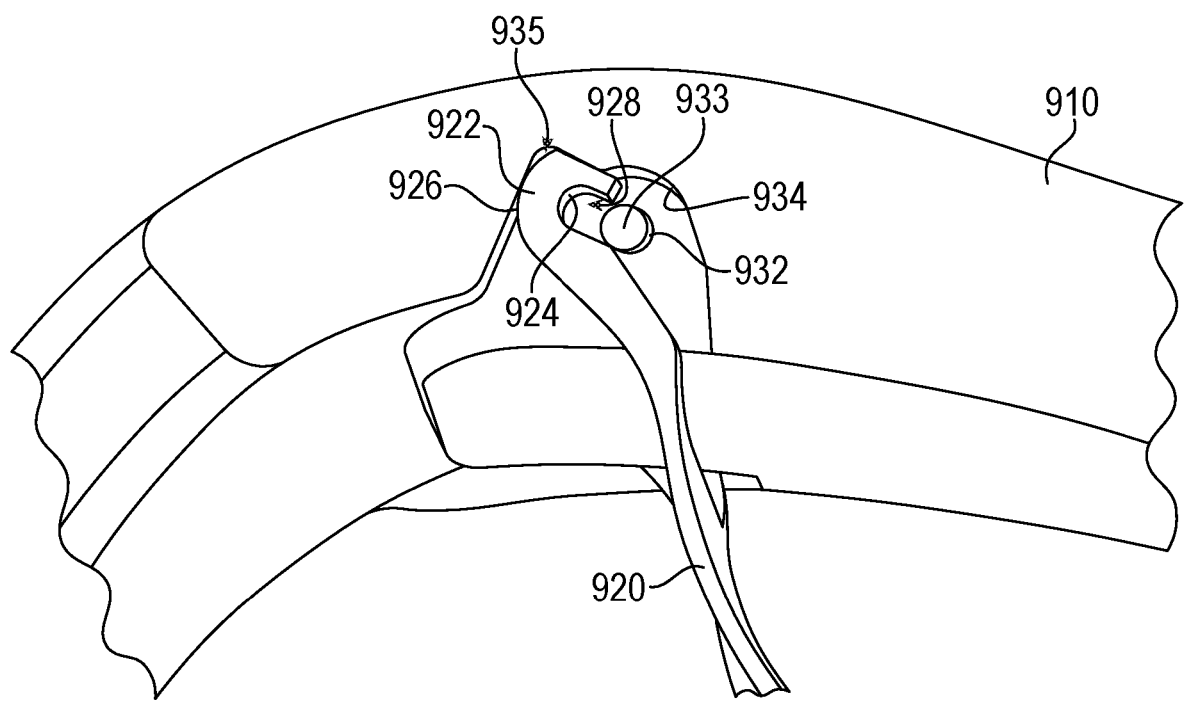
FIG. 41 shows a sectioned view of the hip assembly with the hip wing disconnected from the hinge pin of the rigid housing.

FIG. 41 shows a detailed sectioned view of the hip assembly with the hip wing 920 detached from the rigid housing 910 and the removal mechanism 930 visible. In this case, the removal mechanism is a combination of features that will be described further below. It is noted that more than one removal mechanism 930 may be included on each hip wing 920. For example, the depicted hip wing includes upper and lower attachment portions 921, 923, and each of these attachment portions may include one or more attachment points 925, 927.

The hip wing/removable attachment device 920 includes a hooked hinge portion 922 with an inner hook surface 924 and an outer hook surface 926. The outer hook surface partially circumscribes a rotational axis 933 of the hip wing when the hip wing is attached to the rigid housing.

The inner hook surface 924 engages with the hinge pin 932 and the removable attachment device rotates around the hinge pin when attached to the rigid housing. Optionally, the hinge pin 932 extends axially through the rigid housing 910 and acts as a hinge pin for every attachment point of the hip wing 920. Optionally, the inner and or outer hook surfaces 924, 926 are circular. If the hinge pin is also circular, the inner hook surface 924 may contact the hinge pin along the entire extent of the inner hook surface, or at least the portion thereof that is also circular.

The hook portion 922 has an opening 928 into which the hinge pin 932 passes when attaching and detaching the hip wing 920. This opening 928 is optionally the same width as the diameter of the hinge pin 932, therefore allowing unimpeded attachment and detachment. Alternatively, the opening 928 may be larger and may taper inwardly in order to more easily guide and attach the hooked portion 922 onto the pin 932. Alternatively, the opening may include a portion that is narrower than the hinge pin so as to produce a positive detent snap-connection between the hinge pin 932 and the hook portion 922 via spring-like deformation of the hook portion 922.

The rigid housing 910 includes a radially inward facing hinge guide surface 934 radially offset from and partially circumscribing the hinge pin 932. The outer hook surface 924 may engage the hinge guide surface 934 such that the hooked hinge portion 922 is sandwiched between the hinge pin 932 and the hinge guide surface 934 when the hip wing is attached to the rigid housing.

The rigid housing includes a detachment pocket 935 into which the hooked hinge portion 922 may be slid to disengage the hooked hinge portion from the hinge pin 932 to detach the hip wing from the rigid housing 910. In FIG. 41, the hooked hinge portion 922 is in the detachment pocket 935.

Optionally, the detachment pocket includes a flat wall 936 that acts with a flat portion 929 of the outer hook surface 926 to provide a positive stop for a user when attaching the hip wing to the rigid housing. The detachment pocket 935 is adjacent the guide surface 934 and is deep enough for the hooked hinge portion 922 to clear the hinge pin 932 so as to allow complete removal of the hip wing 920 from the rigid housing 910.

Figure 42:
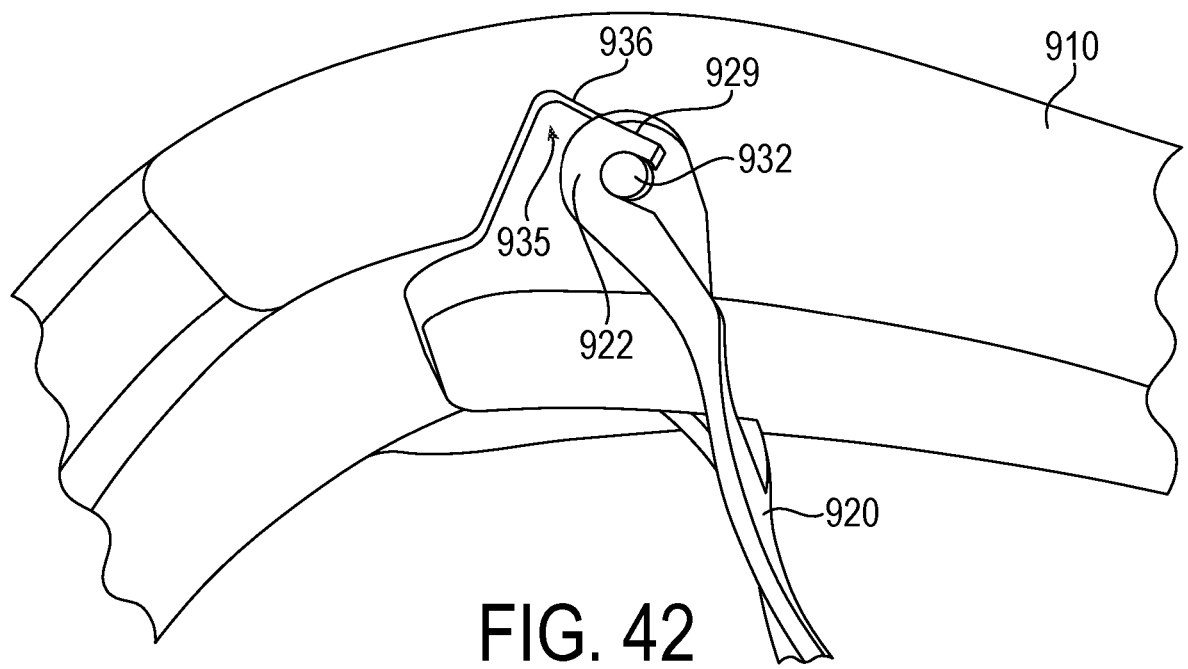
FIG. 42 shows another sectioned view of the hip assembly with the hip wing engaged with the hinge pin.
Figure 43:
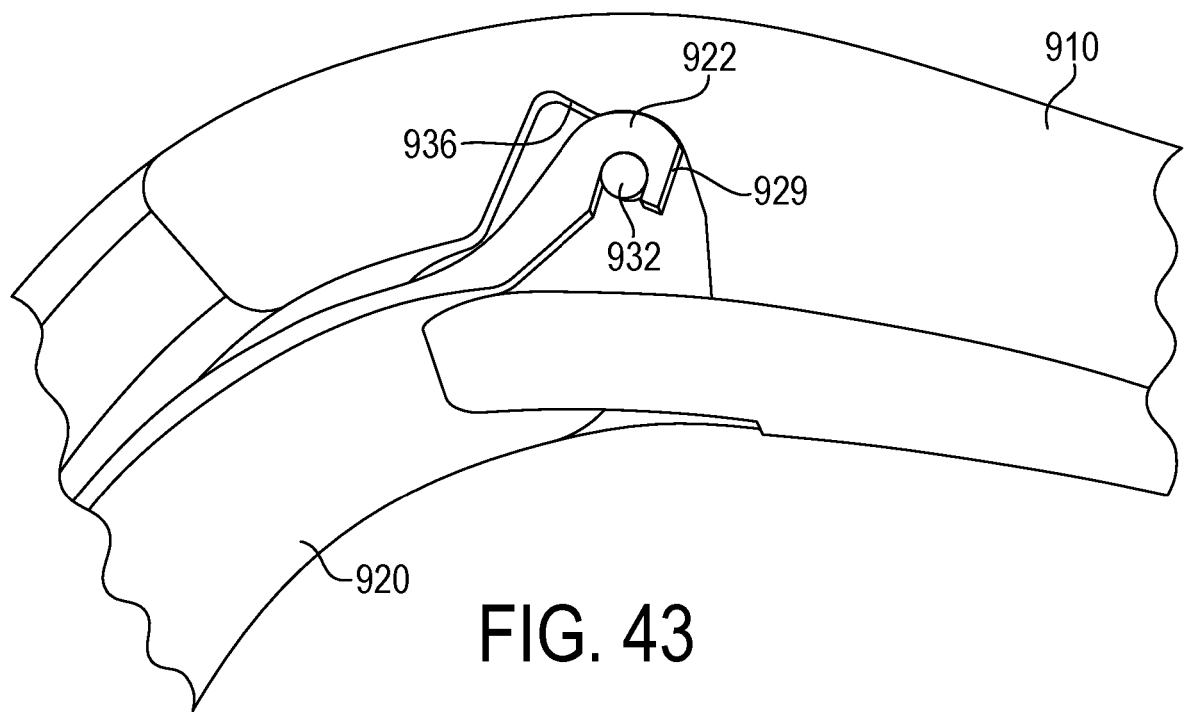
FIG. 43 shows another sectioned view of the hip assembly with the hip wing engaged with the hinge pin and with a guide surface of the rigid housing.

FIG. 42 shows the hip wing being slid onto the hinge pin 932 from the position shown in FIG. 41. FIG. 43 shows the hip wing being rotated out to a "normal" or "operative" position to engage the hooked hinge portion 922 with the guide surface 934 from the position shown in FIG. 42. Removal of the hip wing 920 from the rigid housing 930 may be accomplished by the opposite order of movements shown in FIGS. 41-43. In particular, a method for removing the hip wing includes rotating the hip wing about the hinge pin until the hooked hinge portion 922 is aligned with the pocket 935. This rotational movement is preferably a rotation of the hip wing inward toward the middle of the rigid housing. This movement disengages the hooked hinge portion 922 from the guide surface 934. Once aligned, the hooked hinge portion 922 is slid into the pocket 935 to disengage from the hinge pin 932. Finally, the hip wing 920 may be removed from the rigid housing.

The foregoing manual removal method has the advantage of preventing accidental or purposeful removal of the hip wing during use of the wearable robotic device. In particular, the body of the user would prevent rotation of the hip wing inwardly toward the middle of the rigid housing, therefore, the hooked hinge portion would be prevented from disengaging with the guide surface and the hinge pin.

Figure 44:
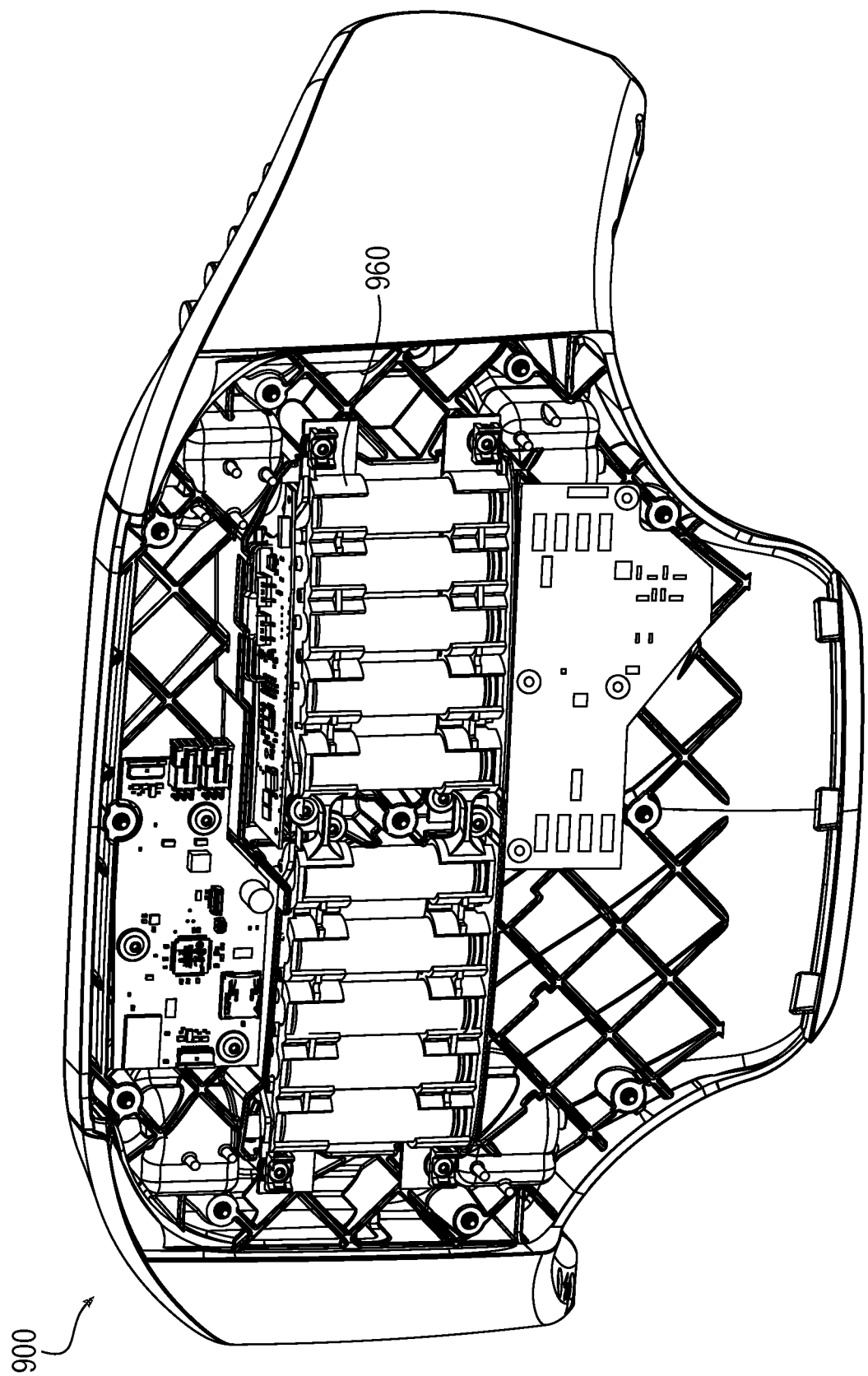
FIG. 44 shows a permanently installed battery with the back cover removed from the hip assembly.
Figure 45:
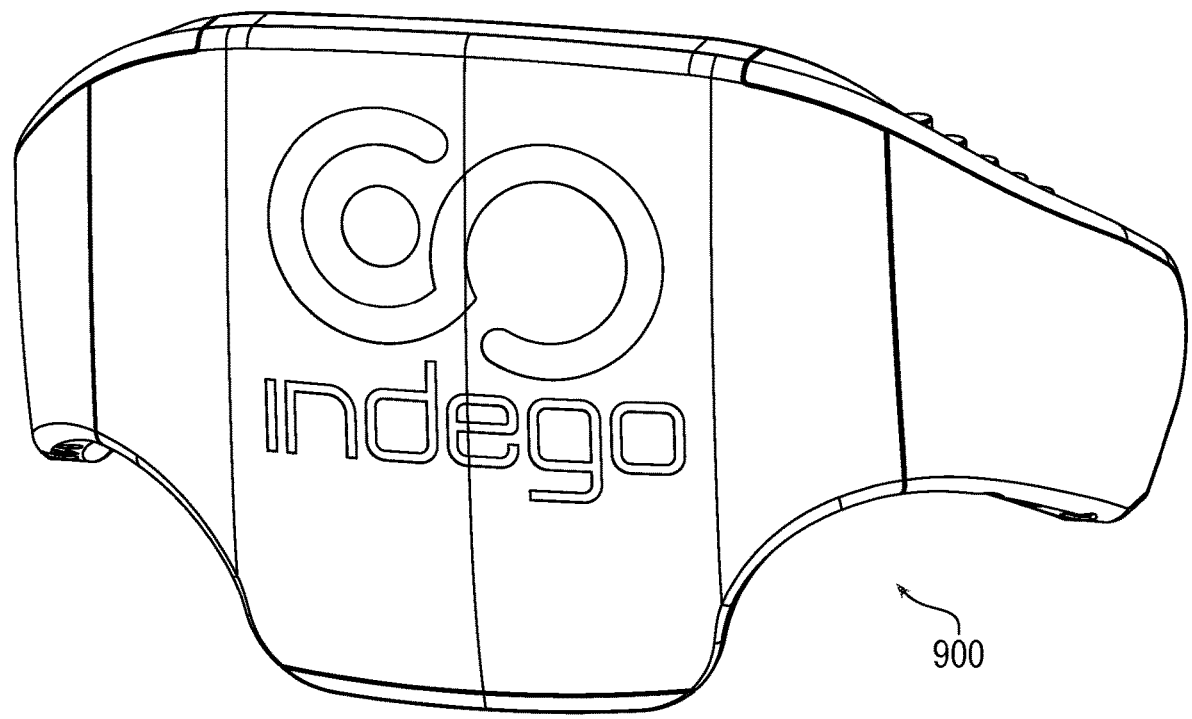
FIG. 45 shows an exemplary hip assembly with a permanently installed battery.

Because this manual removal method and system does not require access to the interior of the rigid housing, exemplary embodiments may optionally include an integral or permanently-installed battery, in contrast to the removable battery described above. FIG. 44 shows such a permanently installed battery 960 in the rigid housing of the hip assembly. FIG. 45 shows an exemplary hip assembly from the back side, and it is evident that the permanently-installed battery allows for the benefit of fewer parts in this assembly (such, as for example, no need for separate battery contacts, a battery lock mechanism, or a battery latch mechanism. Furthermore, the back of the hip assembly is now able to be free of seems, allowing for a cleaner, sleeker look, more surface are for branding, a more easily-cleanable product, and fewer surface discontinuities that could catch on clothing or other environmental objects.

Figure 46:
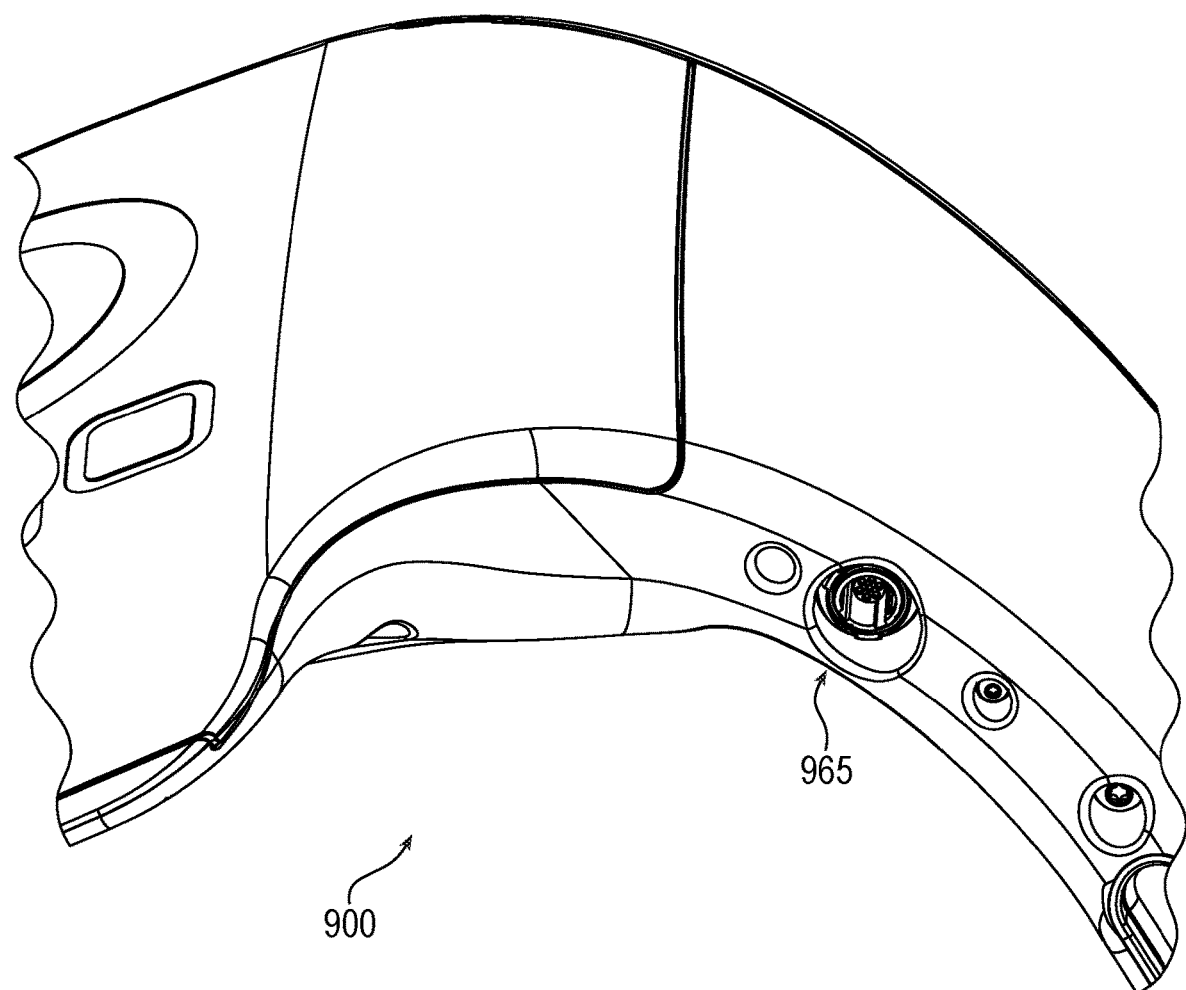
FIG. 46 shows an exemplary hip assembly with a battery charging port located under the hip assembly.

The battery 960 may be charged via a battery port 965 which may be located anywhere that is convenient, but is preferably mounted to an underside of the hip assembly as shown in FIG. 46. An underside mount may have the advantage of preventing debris from the environment (such as, for example, dust and rain) from entering or blocking the battery port 965.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A wearable robotic device comprising:
   a thigh assembly having a first attachment device to secure the thigh assembly to a user's thigh;
   a lower leg assembly rotatably coupled to the thigh assembly at a knee joint, the lower leg assembly including:
   a second attachment device to secure the lower leg assembly to the user's lower leg,
   a lower leg housing, a rigid plantar element,
   a rigid leg element having a lower portion rigidly connected to and extending upwardly from the plantar element, and
   a cam lock device and a manually operated lever that is coupled to the cam lock device, the cam lock device being movable by operation of the manually operated lever;
   wherein the lower portion of the leg element and the plantar element are adjustably coupled to the lower leg housing by the cam lock device and wherein a distance between the knee joint and the plantar element is adjustable by operation of the lever to move the cam lock device,
   so that the cam lock device can lock the distance between the knee joint and plantar element at any distance between minimum and maximum distances.

2. The wearable robotic device of claim 1, wherein the plantar element is made of a thin-sheeted material that is configured to be placed under a sole of a user's foot and fit within a shoe.

3. The wearable robotic device of claim 1, wherein the leg element is made of a thin-sheeted material.

4. The wearable robotic device of claim 1, wherein the thigh assembly and lower leg assembly are coupled by a quick-connect coupler.

5. The wearable robotic device of claim 4, wherein the quick-connect coupler comprises a first portion and a second portion that are drawn together during a coupling operation, and a distance between the first portion of the quick-connect coupler and the plantar element is continuously adjustable between the minimum and maximum distances.

* * * * *